(12) United States Patent
Tomita et al.

(10) Patent No.: US 7,223,581 B2
(45) Date of Patent: May 29, 2007

(54) $F_0F_1$-ATPASE AND DNA ENCODING THE SAME

(75) Inventors: Fusao Tomita, Sapporo (JP); Atsushi Yokota, Sapporo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 343 days.

(21) Appl. No.: 10/694,779

(22) Filed: Oct. 29, 2003

(65) Prior Publication Data

US 2004/0253700 A1    Dec. 16, 2004

Related U.S. Application Data

(62) Division of application No. 09/901,884, filed on Jul. 9, 2001, now abandoned.

(30) Foreign Application Priority Data

Aug. 2, 2000  (JP) .............................. 2000-234317

(51) Int. Cl.
- *C12N 9/16* (2006.01)
- *C12N 15/00* (2006.01)
- *C12N 1/20* (2006.01)
- *C07H 21/04* (2006.01)

(52) U.S. Cl. .................. 435/196; 435/320.1; 435/325; 435/419; 435/252.3; 435/252.32; 435/252.33; 536/23.1; 536/23.32; 536/23.7

(58) Field of Classification Search ..................... None
See application file for complete search history.

(56) References Cited

U.S. PATENT DOCUMENTS 6,022,713 A    2/2000   Noguchi et al. ............... 435/89

FOREIGN PATENT DOCUMENTS

| JP | 54107593 | 8/1979 |
|----|----------|--------|
| JP | 59051799 | 3/1984 |
| WO | 9822614  | 5/1998 |

OTHER PUBLICATIONS

"Introduction to Protein Structure", Braden and Tooze, Garland Publishing Inc., New York, 1991, p. 247.*
Witkowski et al. (1999) Biochemistry 38:11643-11650.*
D. Ivey, et al., "The Abundance of atp Gene Transcript and of the Membrane $F_1F_0$-ATPase as a Function f the Growth pH of Alkaliphilic *Bacillus firmus* OF4", Journal of Bacteriology, vol. 176, No. 16, Aug. 1994, pp. 5167-5170.
M. J. Kullen, et al., "Identification of the pH-Inducible, proton-translocating $F_1F_0$ATPase (atpBEFHAGDC) operon of *Lactobacillus acidophilus* by differential display: gene structure, cloning and characterizati n", Molecular Microbiology, 33(6), 1999, pp. 1152-1161.
P. D. Boyer, "The ATP Synthase—A Splendid Molecular Machine", Annu. Rev. Biochem, 66, 1997, pp. 717-749.
J. E. Walker, et al., "DNA sequence around the *Escherichia coli* unc operon—Completion of the sequ nce of a 17 kilobase segment containing asnA, oriC, unc, glmS and phoS", J. Biochem., 224, 1984, pp. 799-815.
M. Santana, et al., "*Bacillus subtilis* $F_0F_1$ ATPase: DNA Sequence of the atp Operon and Characterization of atp Mutants", Journal of Bacteriology, vol. 176, No. 22, Nov. 1994, pp. 6802-6811.
W. S. A. Brusilow, et al., "Organization and Sequence of the Genes Coding for the Proton-translocating ATPase of *Bacillus megaterium*", The Journal of Biological Chemistry, vol. 264, No. 3, Jan. 25, 1989, pp. 1528-1533.
D. M. Ivey, et al., "Organization and nucleotide sequence of the atp genes encoding the ATP synthase from alkaliphilic *Bacillus firmus* OF4", Mol. Gen. Genet., 229, 1991, pp. 292-300.
S. Ohta, et al., "Sequence and over-expression of subunits of adenosine triphosphate synthas in thermophilic bacterium PS3", Biochimica et Biophysica Acta, 933, 1988, pp. 141-155.
M. Sumi, et al., "$F_0F_1$-ATPase Genes from an Archaebacterium, Methanosarcina barkeri", Biochemical and Biophysical Research Communications, 241, 1997, pp. 427-433.
R. Borghese, et al., "The ATP Synthase atpHAGDC ($F_1$) Operon from *Rhodobacter capsulatus*", Journal of Bacteriology, vol. 180, No. 2, Jan. 1998, pp. 416-421.
R. Borghese, et al., "The atpIBEXF operon coding for the $F_0$ sector of the ATP synthase from th purple nonsulfur photosynthetic bacterium *Rhodobacter capsulatus*", Arch. Microbiol., 170, 1998, pp. 385-388.
S. Kadowaki, et al., "Production of ATP from Adenine by a Combination of Bacterial and Bak r's Yeast Cells", Journal of Fermentation and Bioengineering, vol. 68, No. 6, 1989, pp. 417-422.
H. Sekine, et al., "Cloning and Analysis of $H^+$-ATPase Gene of *Corynebacterium ammoniagenes*", Abstracts of Papers Presented at the Annual Meeting of the Society for Bioscience and Bioengineering, Japan, 2000, p. 80.
F. Tomita, et al., "Cloning and analysis of the atp gene coding for $H^+$-ATPase in *Corynebacterium glutamicum*", Abstracts of Papers Presented at the Annual Meeting of th Society for Bioscience and Bioengineering, Japan, 2000, p. 333.

* cited by examiner

*Primary Examiner*—David J. Steadman
(74) *Attorney, Agent, or Firm*—Antonelli, Terry, Stout & Kraus, LLP.

(57) ABSTRACT

Provided are a protein complex having the $F_0F_1$-ATPase activity; a DNA encoding the protein complex; a method for producing the protein complex, using the DNA; and a method for producing nucleoside 5'-triphosphate using the protein. The present invention further provides a recombinant DNA with the DNA inserted therein; a transformant carrying the recombinant DNA; and a method for producing a protein complex, using the transformant.

15 Claims, 1 Drawing Sheet

Restriction Maps of Fragments Inserted

SEQUENCE LISTING

<160> NUMBER OF SEQ ID NOS: 21

<210> SEQ ID NO 1
<211> LENGTH: 304
<212> TYPE: PRT
<213> ORGANISM: Corynebacterium ammoniagenes

<400> SEQUENCE: 1

Met Cys Asp Gly Val Arg Ser Cys Asp Arg Glu Phe Glu Thr Ser Ile
1               5                   10                  15

Ala Pro Tyr Asp Val Asp Asn Arg Thr Ala Arg Thr Arg Glu Arg Thr
            20                  25                  30

Leu Ser Val Thr Thr Leu Ala Met Lys Gly Ser Phe His Ala Pro Glu
        35                  40                  45

Leu Asp Pro Glu Phe Phe Pro Gly Gln Tyr Tyr Gly Asp Ile Leu Phe
    50                  55                  60

-continued

```
Asp Asp Val Leu Gly Gly Trp Phe Ala Leu Asp Arg Ile Met Leu Val
 65                  70                  75                  80

Arg Leu Leu Met Thr Ala Val Leu Val Leu Leu Phe Ile Ala Ala Phe
                 85                  90                  95

Arg Asn Pro Lys Leu Val Pro Lys Gly Leu Gln Asn Val Ala Glu Tyr
            100                 105                 110

Ala Leu Asp Phe Val Arg Ile His Ile Ala Glu Asp Ile Leu Gly Lys
        115                 120                 125

Lys Glu Gly Arg Arg Phe Leu Pro Leu Leu Ala Ile Phe Phe Gly
130                 135                 140

Thr Leu Phe Trp Asn Val Ser Thr Ile Ile Pro Ala Leu Asn Ile Ser
145                 150                 155                 160

Ala Asn Ala Arg Ile Gly Met Pro Ile Val Leu Ala Gly Ala Ala Tyr
                165                 170                 175

Ile Ala Met Ile Tyr Ala Gly Thr Lys Arg Tyr Gly Phe Gly Lys Tyr
            180                 185                 190

Val Lys Ser Ser Leu Val Ile Pro Asn Leu Pro Pro Ala Leu His Leu
        195                 200                 205

Leu Val Val Pro Ile Glu Phe Phe Ser Thr Phe Ile Leu Arg Pro Val
    210                 215                 220

Thr Leu Ala Ile Arg Leu Met Ala Asn Phe Leu Ala Gly His Ile Ile
225                 230                 235                 240

Leu Val Leu Leu Tyr Ser Ala Thr Asn Phe Phe Phe Trp Gln Leu Asn
                245                 250                 255

Gly Trp Thr Ala Met Ser Gly Val Thr Leu Leu Ala Ala Val Leu Phe
            260                 265                 270

Thr Val Tyr Glu Ile Ile Ile Phe Leu Gln Ala Tyr Ile Phe Ala
        275                 280                 285

Leu Leu Thr Ala Val Tyr Ile Glu Leu Ser Leu His Ala Asp Ser His
    290                 295                 300
```

<210> SEQ ID NO 2
<211> LENGTH: 79
<212> TYPE: PRT
<213> ORGANISM: Corynebacterium ammoniagenes

<400> SEQUENCE: 2

```
Met Asn Asp Ile Ile Leu Ala Gln Ala Thr Glu Thr Ser Phe Asp Gly
  1               5                  10                  15

Leu Gln Ser Ile Gly Tyr Gly Leu Ala Thr Ile Gly Pro Gly Leu Gly
                 20                  25                  30

Ile Gly Ile Leu Val Gly Lys Thr Val Glu Gly Met Ala Arg Gln Pro
            35                  40                  45

Glu Met Ala Gly Gln Leu Arg Thr Thr Met Phe Leu Gly Ile Ala Phe
        50                  55                  60

Val Glu Ala Leu Ala Leu Ile Gly Leu Val Ala Gly Phe Leu Phe
 65                  70                  75
```

<210> SEQ ID NO 3
<211> LENGTH: 189
<212> TYPE: PRT
<213> ORGANISM: Corynebacterium ammoniagenes

<400> SEQUENCE: 3

```
Met Asn Asn Val Phe Tyr Tyr Leu Ala Ala Glu Gly Glu Ser Leu Pro
  1               5                  10                  15
```

```
Leu Glu Gly Gly Asn Ser Leu Leu Phe Pro Lys Ser Tyr Asp Ile Val
                20                  25                  30

Trp Ser Leu Ile Pro Phe Leu Ile Ile Leu Ile Val Phe Ala Met Phe
        35                  40                  45

Val Ile Pro Lys Phe Gln Glu Leu Leu Gln Glu Arg Glu Asp Arg Ile
    50                  55                  60

Glu Gly Gly Ile Lys Arg Ala Glu Ala Gln Gln Ala Glu Ala Lys Ala
 65                 70                  75                  80

Ala Leu Glu Lys Tyr Asn Ala Gln Leu Ala Asp Ala Arg Ala Glu Ala
                85                  90                  95

Ala Glu Ile Arg Glu Gln Ala Arg Glu Arg Gly Lys Gln Ile Glu Ala
            100                 105                 110

Glu Ala Lys Thr Gln Ala Glu Glu Ala Arg Arg Ile Val Ala Gly
        115                 120                 125

Gly Glu Lys Gln Leu Glu Ala Ser Arg Ala Gln Val Val Ala Glu Leu
    130                 135                 140

Arg Ser Asp Ile Gly Gln Asn Ser Ile Asn Leu Ala Glu Lys Leu Leu
145                 150                 155                 160

Gly Gly Glu Leu Ser Glu Ser Thr Lys Gln Ser Ser Thr Ile Asp Asn
                165                 170                 175

Phe Leu Ser Glu Leu Asp Ser Val Ala Ser Ala Gly Lys
            180                 185

<210> SEQ ID NO 4
<211> LENGTH: 271
<212> TYPE: PRT
<213> ORGANISM: Corynebacterium ammoniagenes

<400> SEQUENCE: 4

Met Lys Ala Ala Ser Arg Glu Ser Leu Ala Ser Ala Thr Glu Ser Leu
 1               5                  10                  15

Asp Ser Asn Leu Ala Ala Gln Ala Gly Val Ala Val Ser Thr Met Thr
                20                  25                  30

Gly Met Glu Leu Phe Glu Val Ser Gln Val Leu Gly Asp Asp Arg Glu
            35                  40                  45

Leu Arg Gly Ala Val Ile Asp Glu Ser Ala Ser Thr Glu Ser Arg Lys
    50                  55                  60

Lys Leu Val Asn Asp Leu Phe Gly Ala Lys Val Ser Pro Ala Thr Leu
 65                 70                  75                  80

Gln Val Leu Glu Gln Ile Ala Ser Ser Lys Trp Ser Ser Ala Arg Glu
                85                  90                  95

Met Val Ser Gly Leu Ile Ala Leu Ser Arg Arg Ala Leu Met Arg Gly
            100                 105                 110

Ala Glu Ser Glu Gly Gln Leu Gly Gln Val Glu Asp Glu Leu Phe Arg
        115                 120                 125

Leu Ser Arg Ile Leu Asp Arg Glu Gly Glu Leu Thr Gln Leu Leu Ser
    130                 135                 140

Asp Arg Ala Ala Glu Pro Ala Arg Lys Arg Lys Leu Leu Ala Asp Val
145                 150                 155                 160

Leu Tyr Gly Lys Val Thr Lys Phe Thr Glu Ala Leu Ala Leu Gln Val
                165                 170                 175

Ile Asp Arg Pro Glu His Asn Pro Ile Asp Ile Ala Asn Leu Ala
            180                 185                 190

Ala Glu Ala Ala Gln Leu Gln Gly Arg Thr Val Ala His Val Val Ser
        195                 200                 205
```

```
Ala Gly Glu Leu Asn Glu Gly Gln Gln Ala Val Leu Ala Glu Lys Leu
        210                 215                 220

Gly Lys Ile Tyr Gly Arg Ala Met Ser Ile His Ser Glu Val Asp Thr
225                 230                 235                 240

Ser Leu Leu Gly Gly Met Thr Ile Arg Val Gly Asp Glu Val Ile Asp
                245                 250                 255

Gly Ser Thr Ala Gly Lys Ile Glu Arg Leu Arg Thr Ala Leu Lys
        260                 265                 270

<210> SEQ ID NO 5
<211> LENGTH: 546
<212> TYPE: PRT
<213> ORGANISM: Corynebacterium ammoniagenes

<400> SEQUENCE: 5

Met Ala Glu Leu Thr Ile Ser Ser Asp Glu Ile Arg Ser Ala Ile Ala
1               5                   10                  15

Asn Tyr Thr Ser Ser Tyr Ser Ala Glu Ala Ser Arg Glu Glu Val Gly
                20                  25                  30

Val Val Ile Ser Ala Ala Asp Gly Ile Ala Gln Val Ser Gly Leu Pro
            35                  40                  45

Ser Val Met Ala Asn Glu Leu Leu Glu Phe Pro Gly Gly Val Ile Gly
        50                  55                  60

Val Ala Gln Asn Leu Glu Thr Asn Ser Ile Gly Val Val Ile Leu Gly
65                  70                  75                  80

Asn Tyr Glu Ser Leu Lys Glu Gly Asp Gln Val Lys Arg Thr Gly Glu
                85                  90                  95

Val Leu Ser Ile Pro Val Gly Glu Glu Phe Leu Gly Arg Val Ile Asn
            100                 105                 110

Pro Leu Gly Gln Ala Ile Asp Gly Leu Gly Pro Ile Ala Gly Glu Glu
        115                 120                 125

Asp Arg Val Leu Glu Leu Gln Ala Pro Ser Val Leu Gln Arg Gln Pro
130                 135                 140

Val Glu Glu Pro Met Gln Thr Gly Ile Lys Ala Ile Asp Ala Met Thr
145                 150                 155                 160

Pro Ile Gly Arg Gly Gln Arg Gln Leu Ile Ile Gly Asp Arg Lys Thr
                165                 170                 175

Gly Lys Thr Ala Val Cys Ile Asp Thr Ile Leu Asn Gln Lys Ala Asn
            180                 185                 190

Trp Glu Ser Gly Asp Lys Asn Lys Gln Val Arg Cys Ile Tyr Val Ala
        195                 200                 205

Ile Gly Gln Lys Gly Ser Thr Ile Ala Gly Val Arg Lys Thr Leu Glu
        210                 215                 220

Glu Gln Gly Ala Leu Glu Tyr Thr Thr Ile Val Ala Ala Pro Ala Ser
225                 230                 235                 240

Asp Ser Ala Gly Phe Lys Trp Leu Ala Pro Phe Ser Gly Ala Ala Leu
                245                 250                 255

Gly Gln His Trp Met Tyr Gln Gly Asn His Val Leu Val Ile Tyr Asp
            260                 265                 270

Asp Leu Thr Lys Gln Ala Glu Ala Tyr Arg Ala Ile Ser Leu Leu Leu
        275                 280                 285

Arg Arg Pro Pro Gly Arg Glu Ala Tyr Pro Gly Asp Val Phe Tyr Leu
290                 295                 300

His Ser Arg Leu Leu Glu Arg Ala Ala Lys Leu Ser Asp Asp Leu Gly
```

```
                    305                 310                 315                 320
Ala Gly Ser Leu Thr Ala Leu Pro Ile Ile Glu Thr Lys Ala Asn Asp
                325                 330                 335

Val Ser Ala Phe Ile Pro Thr Asn Val Ile Ser Ile Thr Asp Gly Gln
            340                 345                 350

Val Phe Leu Glu Ser Asp Leu Phe Asn Gln Gly Val Arg Pro Ala Ile
        355                 360                 365

Asn Val Gly Val Ser Val Ser Arg Val Gly Gly Ala Ala Gln Thr Lys
    370                 375                 380

Gly Met Lys Lys Val Ala Gly Asn Leu Arg Leu Asp Leu Ala Ser Tyr
385                 390                 395                 400

Arg Asp Leu Gln Gly Phe Ala Ala Phe Ala Ser Asp Leu Asp Pro Val
                405                 410                 415

Ser Lys Ala Gln Leu Glu Arg Gly Glu Arg Leu Val Glu Ile Leu Lys
            420                 425                 430

Gln Ser Glu Ser Ser Pro Gln Ala Val Glu Tyr Gln Met Val Ser Ile
        435                 440                 445

Phe Leu Ala Glu Glu Gly Val Phe Asp Val Val Pro Val Glu Asp Val
    450                 455                 460

Arg Arg Phe Glu Ala Asp Val Gln Glu Tyr Leu Gln Gln Asn Thr Pro
465                 470                 475                 480

Glu Val Tyr Glu Gln Ile Ala Gly Gly Lys Ala Phe Thr Asp Glu Ser
                485                 490                 495

Lys Glu Ala Leu Leu Ala Ala Lys Asp Phe Thr Pro Ser Phe Arg
            500                 505                 510

Thr Thr Glu Gly His Asn Leu Gly Thr Glu Ala Pro Val Asp Pro Leu
        515                 520                 525

Ala Glu Glu Glu Val Lys Lys Thr Glu Val Thr Val Ser Arg Lys Ser
    530                 535                 540

Ala Lys
545

<210> SEQ ID NO 6
<211> LENGTH: 327
<212> TYPE: PRT
<213> ORGANISM: Corynebacterium ammoniagenes

<400> SEQUENCE: 6

Met Ala Asn Leu Arg Glu Leu Arg Asp Arg Ile Arg Ser Val Asn Ser
  1               5                  10                  15

Thr Lys Lys Ile Thr Lys Ala Gln Glu Leu Ile Ala Thr Ser Arg Ile
             20                  25                  30

Thr Lys Ala Gln Ala Lys Val Asp Ala Ala Pro Tyr Ala His Glu
         35                  40                  45

Met Ser Asn Met Met Asp Arg Leu Ala Ser Ala Ser Ser Leu Glu His
     50                  55                  60

Pro Met Leu Arg His Arg Glu Asn Gly Lys Val Ala Ala Val Leu Val
 65                  70                  75                  80

Val Ser Ser Asp Arg Gly Met Cys Gly Gly Tyr Asn Asn Val Phe
                 85                  90                  95

Lys Lys Ala Ala Glu Leu Glu Gly Leu Leu Arg Gly Gln Gly Phe Asp
            100                 105                 110

Val Val Arg Tyr Val Thr Gly Ser Lys Gly Val Gly Tyr Tyr Asn Phe
        115                 120                 125
```

-continued

```
Arg Glu Lys Glu Val Val Gly Ala Trp Thr Gly Phe Ser Gln Asp Pro
        130                 135                 140

Ser Trp Glu Gly Thr His Asp Val Arg His His Leu Val Asp Gly Phe
145                 150                 155                 160

Ile Ala Gly Ser Glu Gly Thr Thr Pro Ala Arg Gln Gly Val Asn Thr
                165                 170                 175

Glu Asp Gln Thr Val Arg Gly Phe Asp Gln Val His Val Val Tyr Thr
            180                 185                 190

Glu Phe Glu Ser Met Leu Val Gln Thr Pro Arg Ala His Gln Leu Leu
        195                 200                 205

Pro Ile Glu Pro Val Ile Lys Glu Glu Leu His Leu Gly Asp Ser
210                 215                 220

Ala Leu Glu Ala Asn Pro Asp Ala Gln Gly Leu Ser Ala Asp Tyr Glu
225                 230                 235                 240

Phe Glu Pro Asp Ala Asp Thr Leu Leu Ser Ala Leu Leu Pro Gln Tyr
                245                 250                 255

Val Ser Arg Ile Leu Phe Ser Met Phe Leu Glu Ala Ser Ala Ser Glu
            260                 265                 270

Ser Ala Ala Arg Arg Thr Ala Met Lys Ala Ala Thr Asp Asn Ala Asn
        275                 280                 285

Asp Leu Val Thr Asp Leu Ser Arg Val Ala Asn Gln Ala Arg Gln Ala
290                 295                 300

Gln Ile Thr Gln Glu Ile Thr Glu Ile Val Gly Gly Ala Gly Ala Leu
305                 310                 315                 320

Ala Glu Ser Ala Glu Ser Asp
                325
```

<210> SEQ ID NO 7
<211> LENGTH: 481
<212> TYPE: PRT
<213> ORGANISM: Corynebacterium ammoniagenes

<400> SEQUENCE: 7

```
Met Thr Thr Ala Leu His Glu Gln Asn Thr Gln Glu Ser Ala Ile Ala
1               5                   10                  15

Gly Arg Val Val Arg Val Ile Gly Pro Val Val Asp Val Glu Phe Pro
            20                  25                  30

Arg Gly Gly Leu Pro Ala Leu Tyr Asn Ala Leu Thr Val Glu Ile Asn
        35                  40                  45

Leu Glu Ser Val Ala Arg Thr Ile Thr Leu Glu Val Ala Gln His Leu
    50                  55                  60

Gly Asp Asn Leu Val Arg Thr Val Ser Met Ala Pro Thr Asp Gly Leu
65                  70                  75                  80

Val Arg Arg Ala Ala Val Thr Asp Thr Glu Ala Pro Ile Ser Val Pro
                85                  90                  95

Val Gly Asp Val Val Lys Gly His Val Phe Asn Ala Leu Gly Asp Cys
            100                 105                 110

Leu Asp Glu Pro Gly Leu Gly Arg Asp Gly Glu Gln Trp Gly Ile His
        115                 120                 125

Arg Glu Pro Pro Ala Phe Asp Gln Leu Glu Gly Lys Thr Glu Ile Leu
    130                 135                 140

Glu Thr Gly Ile Lys Val Ile Asp Leu Leu Thr Pro Tyr Val Lys Gly
145                 150                 155                 160

Gly Lys Ile Gly Leu Phe Gly Gly Ala Gly Val Gly Lys Thr Val Leu
                165                 170                 175
```

```
Ile Gln Glu Met Ile Thr Arg Ile Ala Arg Glu Phe Ser Gly Thr Ser
            180                 185                 190

Val Phe Ala Gly Val Gly Glu Arg Thr Arg Glu Gly Thr Asp Leu Phe
        195                 200                 205

Leu Glu Met Glu Glu Met Gly Val Leu Gln Asp Thr Ala Leu Val Phe
        210                 215                 220

Gly Gln Met Asp Glu Pro Pro Gly Val Arg Met Arg Val Ala Leu Ser
225                 230                 235                 240

Gly Leu Thr Met Ala Glu Tyr Phe Arg Asp Val Gln Asn Gln Asp Val
            245                 250                 255

Leu Leu Phe Ile Asp Asn Ile Phe Arg Phe Thr Gln Ala Gly Ser Glu
            260                 265                 270

Val Ser Thr Leu Leu Gly Arg Met Pro Ser Ala Val Gly Tyr Gln Pro
        275                 280                 285

Thr Leu Ala Asp Glu Met Gly Val Leu Gln Glu Arg Ile Thr Ser Thr
        290                 295                 300

Lys Gly Lys Ser Ile Thr Ser Leu Gln Ala Val Tyr Val Pro Ala Asp
305                 310                 315                 320

Asp Tyr Thr Asp Pro Ala Pro Ala Thr Thr Phe Ala His Leu Asp Ala
            325                 330                 335

Thr Thr Glu Leu Asp Arg Ala Ile Ala Ser Lys Gly Ile Tyr Pro Ala
            340                 345                 350

Val Asn Pro Leu Ser Ser Thr Ser Arg Ile Leu Glu Pro Ser Ile Val
        355                 360                 365

Gly Glu Arg His Tyr Ala Val Ala Gln Arg Val Ile Asn Ile Leu Gln
        370                 375                 380

Lys Asn Lys Glu Leu Gln Asp Ile Ile Ala Ile Leu Gly Met Asp Glu
385                 390                 395                 400

Leu Ser Glu Glu Asp Lys Ile Thr Val Gln Arg Ala Arg Arg Ile Glu
            405                 410                 415

Arg Phe Leu Gly Gln Asn Phe Phe Val Ala Glu Lys Phe Thr Gly Leu
            420                 425                 430

Pro Gly Ser Tyr Val Pro Leu Ala Asp Thr Ile Asp Ala Phe Glu Arg
        435                 440                 445

Ile Cys Asn Gly Glu Phe Asp His Tyr Pro Glu Gln Ala Phe Asn Gly
        450                 455                 460

Leu Gly Gly Leu Asp Asp Val Glu Ala Ala Tyr Lys Lys Leu Thr Glu
465                 470                 475                 480

Lys

<210> SEQ ID NO 8
<211> LENGTH: 123
<212> TYPE: PRT
<213> ORGANISM: Corynebacterium ammoniagenes

<400> SEQUENCE: 8

Met Ala Asp Ile Thr Val Glu Leu Val Ser Val Glu Arg Met Leu Trp
1               5                   10                  15

Ser Gly Lys Ala Thr Ile Ile Ser Ala Glu Thr Thr Glu Gly Glu Ile
            20                  25                  30

Gly Val Leu Pro Gly His Glu Pro Leu Leu Gly Gln Leu Ala Glu Asn
        35                  40                  45

Gly Val Val Thr Phe Arg Pro Val Asp Gly Asp Arg Lys Val Ala Ala
    50                  55                  60
```

```
Val Gln Gly Gly Phe Leu Ser Val Ser Thr Glu Lys Ile Thr Val Leu
 65                  70                  75                  80

Ala Asp Trp Ala Val Trp Ala Asp Glu Val Asn Glu Ser Gln Ala Gln
             85                   90                  95

Glu Asp Ala Leu Ser Ser Asp Glu Leu Val Ser Ser Arg Gly Gln Ala
            100                 105                 110

Ala Leu Arg Ala Leu Ala Arg Ser Arg Glu Ser
        115                 120

<210> SEQ ID NO 9
<211> LENGTH: 912
<212> TYPE: DNA
<213> ORGANISM: Corynebacterium ammoniagenes

<400> SEQUENCE: 9
atgtgcgacg gagtccgtag ctgtgacaga gagtttgaga cgtccatcgc accgtacgac       60
gtcgacaatc gtacggcccg aacacgggag agaacgctga gcgttacaac attggccatg      120
aagggtagct tccacgcgcc cgaactggac cagaattttt cccggggca atattacggc       180 gacatcctgt tcgacgatgt gttgggcgga tggttcgcac ttgatcgcat catgctggtt      240
cgtctgttga tgaccgccgt cttggtgctt ttatttattg cagcatttag gaacccaaag      300
ctggttccta aggactaca gaacgtcgca gaatacgcgt tagatttcgt ccgaattcac       360
attgctgagg acatcctggg caagaaggag ggtcgtcgct tcctaccgtt gctggcggct      420
atcttcttcg gcacccttt ctggaacgtc tccacgatta ttccggcact gaacatctcc      480
gcaaacgctc gtattggcat gcctattgtc ttggctggcg cagcgtatat cgcaatgatt      540
tacgcaggca ccaagcgcta tggcttcggt aagtacgtca agtcgtcgtt ggttattcct      600
aaccttccac cggctttgca cttgctggtt gttccaattg agttttttctc gaccttcatc      660 ttgcgtcccg tcactctggc aattcgtctt atggcgaact tccttgccgg ccacatcatt      720
ttggttctgc tgtactctgc cacgaacttc ttcttctggc agctcaacgg ctggacagcg      780
atgtccggtg tgaccctgct cgcagcggtt ctgtttacgg tctacgagat catcatcatc      840
ttcctgcagg catacatctt tgctctgctg acggcggtgt acatcgagtt gtcacttcac      900
gcagactcgc ac                                                          912

<210> SEQ ID NO 10
<211> LENGTH: 237
<212> TYPE: DNA
<213> ORGANISM: Corynebacterium ammoniagenes

<400> SEQUENCE: 10
atgaacgaca tcatcttggc tcaggcaacc gagacctcct tcgatggcct tcagtccatc       60
ggctacggcc ttgcaaccat cggccctggc ttgggtattg gtatcctcgt cggcaagacc      120
gttgagggca tggcacgtca gcctgagatg gctggccagc tgcgtaccac catgttcctg      180
ggtatcgcct tcgttgaggc tcttgcactt atcggcctgg ttgcaggctt cctgttc         237

<210> SEQ ID NO 11
<211> LENGTH: 567
<212> TYPE: DNA
<213> ORGANISM: Corynebacterium ammoniagenes

<400> SEQUENCE: 11
atgaacaacg tcttttacta tcttgcagcg gaaggagagt cccttccact ggaaggtggc       60
```

-continued

```
aactcccttc tgtttcccaa gagctatgac atcgtctggt ctctgatccc gttcttaatc      120
atccttattg tcttcgcaat gtttgtcatt ccgaagttcc aggaactgtt gcaagagcgt      180
gaagaccgga ttgagggcgg catcaagcgc gctgaagccc aacaggcaga agcaaaggcc      240
gcacttgaga agtacaacgc acagctagct gacgctcgcg cagaggcagc tgaaatccgt      300
gagcaggcgc gtgagcgcgg caagcagatt gaagcagagg caaagaccca ggcagaggaa      360
gaagcacgcc gtatcgtcgc aggtggcgaa aaacagcttg aagcttcccg cgcacaggta      420
gttgctgaac tgcgttccga tatcggacag aactccatca acttggctga agctgctc       480 ggcggtgaac tctctgagtc caccaagcag tcttcaacca ttgataactt cctgtccgag      540
ctcgactctg tggcatcggc cggaaag                                          567
```

<210> SEQ ID NO 12
<211> LENGTH: 813
<212> TYPE: DNA
<213> ORGANISM: Corynebacterium ammoniagenes

<400> SEQUENCE: 12

```
atgaaggcag ctagccgcga atcgctcgca tccgctaccg agtcgctgga ttccaatctg       60
gcagctcaag caggtgtagc agtgtccacc atgaccggca tggaactgtt cgaggtttcc      120
caagtattgg gtgatgaccg cgaactccgt ggagcagtca ttgatgaatc tgcttccact      180
gaatcccgca agaagctcgt taatgatctc ttcggtgcca agtttctcc tgctaccttg       240 caggttctgg aacagattgc atcgtcgaag tggtcgagcg cccgcgagat ggtttccgga      300
ctgatcgctc tttcacgtcg tgctttgatg cgcggcgcag aaagcgaagg acaactagga      360
caggtcgaag atgaactctt ccgcttgtcc cggatcctgg accgcgaagg cgaactcacc      420
cagctgcttt ctgaccgagc tgcagaacct gcgcgtaagc gcaagttgct ggcagatgtg      480
ctttacggaa aggtcaccaa attcactgag gcgcttgcgc tgcaggtgat tgaccgccct      540
gagcacaatc ccattgatga cattgcgaat ctggcggctg aagcagcaca gcttcagggt      600
cgcactgttg cgcacgttgt tagtgcgggt gaactcaatg aaggccagca ggcagtactc      660
gccgagaagc tgggcaagat ttatggtcgt gcgatgtcca tccactctga ggttgacacc      720
agcctcctcg gtggtatgac aatccgcgta ggcgatgaag ttattgacgg ttctaccgca      780
ggcaaaattg agcgcctgcg tacccgctttg aag                                  813
```

<210> SEQ ID NO 13
<211> LENGTH: 1638
<212> TYPE: DNA
<213> ORGANISM: Corynebacterium ammoniagenes

<400> SEQUENCE: 13

```
atggcggagc tgacgatctc ctccgatgag atccgtagcg cgatagcgaa ctacacctcg       60
agctactccg cggaggcctc ccgtgaggag gtcggcgtgg tcatttcggc agctgacggt      120
attgcacagg tttctgggct accttcagtt atggcgaatg agctgctcga gttccctggc      180
ggcgtaatcg gcgtcgcaca aaaccttgaa accaactcca ttggcgttgt tattcttggt      240
aactacgagt ccctcaaaga aggcgaccaa gttaagcgaa ctggcgaagt tctctccatc      300
ccagtgggtg aagagttcct cggccgcgtt attaacccat gggtcaggc aattgacggc      360 ctgggcccaa tcgctggcga agaggaccgc gtcctcgagc tgcaggcacc ttccgtgttg      420
cagcgtcagc cagttgaaga gccaatgcag accggcatca aggctattga tgctatgacc      480
ccaatcggtc gcggtcagcg tcagctcatc attggtgacc gtaagactgg taaaaccgca      540
```

-continued

```
gtctgcatcg acaccatcct taaccagaag gctaactggg aatccggcga caagaacaag      600
caagttcgtt gtatctacgt cgctattggt cagaagggct ccaccatcgc tggtgtccgc      660
aagaccctcg aagagcaggg cgctctggag tacaccacca tcgtggctgc tcctgcttct      720
gactccgcgg gcttcaagtg gttggcacca ttctccggtg ctgctcttgg tcagcactgg      780
atgtaccagg gcaaccacgt cttggtcatc tatgatgact tgaccaagca ggctgaggct      840
taccgtgcga tttccctgtt gctgcgtcgc ccgccgggcc gcgaagctta cccaggtgac      900
gtcttctact gcactcccg tctgctggag cgtgctgcga agctctccga tgatttgggt      960
gcaggttctt tgaccgcact gccaattatt gaaaccaagg cgaatgacgt gtctgcgttc     1020
attccaacca acgttatttc cattaccgac ggccaggtct tcctggagtc cgacctgttc     1080
aaccaaggcg tccgtccggc aattaacgtc ggtgtgtcgg tttcccgtgt tggtggcgct     1140
gctcagacca agggtatgaa gaaggttgca ggtaacctgc gtcttgacct cgcttcctac     1200
cgtgatctgc agggctttgc tgccttcgct tctgacttgg acccagtgtc caaggcccag     1260
cttgagcgcg gtgagcgtct ggttgagatc ctgaagcagt ctgagtcttc tcctcaggca     1320
gtcgagtacc agatggtttc catcttcttg gctgaagaag gcgtcttcga cgtcgttcct     1380
gtcgaagatg ttcgtcgctt tgaggctgac gttcaggaat acctgcagca gaacacccca     1440
gaggtttacg agcagattgc cggcggtaag gcatttaccg acgagtccaa ggaagccctg     1500
ttggctgcag ctaaggactt cactccttcc ttccgcacca ccgagggcca caacttgggc     1560
actgaagctc cagttgatcc tttggctgaa gaagaagtca agaagactga agtcaccgtc     1620
tcccgtaagt cggctaag                                                  1638
```

<210> SEQ ID NO 14
<211> LENGTH: 981
<212> TYPE: DNA
<213> ORGANISM: Corynebacterium ammoniagenes

<400> SEQUENCE: 14

```
atggcaaatc ttcgcgaatt gcgcgaccgt atccggtccg tgaactcgac caagaagatc       60
accaaggcgc aggagctgat tgcaacttct cgcattacca aggcgcaagc caaggttgat      120
gcagcagcac cgtacgcaca cgagatgtcg aacatgatgg accgtcttgc atcggctagc      180
tcgttggagc acccaatgct gcgccaccgt gaaaacggca agttgcagc cgtactcgtg      240 gtctcttctg accgcggtat gtgtggtggc tacaacaaca acgtctttaa gaaggctgct      300
gagctcgaag gactccttcg cggtcaaggc ttcgacgttg tccgctacgt aaccggtagc      360
aagggcgtcg gctactacaa cttccgtgag aggaagttg tgggcgcgtg gactggcttt      420
tctcaggatc cgtcctggga aggcactcac gacgttcgtc accacttggt tgacggcttc      480
attgctggct ccgaaggtac aactccggcc cgtcagggcg tgaacaccga agaccaaacg      540
gtacgtggtt tcgaccaggt acacgttgtt tacaccgagt tcgaatccat gctggttcag      600
actccacgtg ctcaccagtt gttgccgatt gaaccggtaa ttaaagaaga ggaacttcac      660
ctgggcgact cggcgctaga agccaaccct gatgctcagg gcctgtctgc tgactacgag      720
tttgagccgg atgcagatac tttgctctcg gcacttctgc cgcagtatgt atcacgtatc      780
cttttctcga tgttcttgga ggcttcggct tctgagtccg cagctcgtcg aactgcaatg      840
aaggctgcga ctgacaacgc taatgacttg gtaaccgact tgtctcgtgt tgctaaccag      900
gctcgtcagg cgcagattac ccaggaaatc acagaaatcg tcggtggcgc tggcgcgctc      960
```

```
gccgaaagcg cagaaagtga c                                          981
```

<210> SEQ ID NO 15
<211> LENGTH: 1443
<212> TYPE: DNA
<213> ORGANISM: Corynebacterium ammoniagenes

<400> SEQUENCE: 15

```
atgactacag ctctgcatga gcagaacaca caggagtcgg caattgccgg ccgtgtggtg    60
cgtgtcatcg gtccggtcgt cgacgtggag ttcccgcgtg gcggactacc ggcactgtat   120
aatgcactga ccgtcgagat taacctcgag tctgttgcac gcaccattac ccttgaggtt   180
gcacagcacc tcggcgacaa cctggttcgt accgtttcga tggcacctac cgatggtctt   240
gttcggcgtg cggcagtaac cgataccgag gcaccaatct ccgtgccagt tggcgatgtt   300
gttaagggcc acgtctttaa cgcattgggc gactgcttgg atgagccagg tctgggccgc   360
gatggcgagc agtggggcat ccaccgcgag ccaccagcat cgaccagct cgaaggcaag   420
accgagatcc tcgaaaccgg cattaaggtc atcgacctt tgaccccata cgtcaagggc   480
ggcaagattg gcctcttcgg cggtgcgggt gttggtaaga ccgttctgat tcaggaaatg   540
attactcgta tcgcacgcga gttctctggt acctccgtgt cgctggtgt tggcgagcgt   600
acccgtgagg gcaccgacct gttcttggaa atggaagaaa tgggcgtact gcaggacacc   660
gccctcgtgt tcggccagat ggacgaaccg ccaggagttc gtatgcgcgt agctctgtcc   720
ggtctgacca tggcggagta cttccgcgat gttcagaacc aggacgtgct gctgttcatc   780
gataacatct tccgtttcac tcaggctggt tctgaagttt cgacccttct gggccgtatg   840
ccttccgctg tgggctacca gccaaccttg gctgatgaga tgggtgtact ccaggagcgc   900
attacctcta ctaagggtaa gtcgattacc tctctgcagg ccgtttacgt tcctgccgat   960
gactacactg acccagctcc agcgaccacc ttcgctcact tggatgcaac caccgagctt  1020
gaccgtgcga ttgcttccaa gggtatctac ccagcagtga acccactgtc gtcgacttct  1080
cgtattctcg agccaagcat cgtcggtgag cgtcactacg ctgttgctca gcgcgtgatc  1140
aacattttgc agaagaacaa ggaactgcag gatattatcg cgattctggg tatggacgag  1200
ctgtctgaag aggacaagat caccgttcag cgcgcacgtc gcattgagcg cttcttgggc  1260
cagaacttct tcgtcgcaga aagttcacc ggcctgccag gctcttacgt acctttggca  1320
gataccatcg acgctttcga gcgcatttgc aacggcgaat cgaccacta cccagagcag  1380
gccttcaacg gcttgggtgg cttggacgac gtcgaagcag cgtacaagaa gctgactgag  1440
aag                                                               1443
```

<210> SEQ ID NO 16
<211> LENGTH: 369
<212> TYPE: DNA
<213> ORGANISM: Corynebacterium ammoniagenes

<400> SEQUENCE: 16

```
atggctgaca tcaccgtgga actggttct gttgagcgca tgctgtggtc tggaaaggcc    60
accatcattt ccgcagagac caccgagggt gagatcggcg tgcttccggg tcacgaacca   120
ttgcttggcc agctggctga gaatggcgta gttaccttcc gtcctgtcga cggtgaccgc   180
aaggtcgccg ctgttcaggg tggcttcctc tccgtatcca ccgagaagat caccgtcttg   240
gcggactggg cagtttgggc agatgaggtt aatgaatctc aggctcaaga agatgccttg   300
tcttccgatg aattggtttc ttctcgtgga caggcagcgc ttcgcgcctt ggctcgttcc   360
```

```
cgcgaaagc                                                              369

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
acgttctgct gttcgttgac                                                   20

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
ccggtgaata cttctgc                                                      17

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
tggttgcagg cttcctgttc                                                   20

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
ctgcttcaat ctgcttg                                                      17

<210> SEQ ID NO 21
<211> LENGTH: 9500
<212> TYPE: DNA
<213> ORGANISM: Corynebacterium ammoniagenes
<220> FEATURE:
<221> NAME/KEY: CDS
<222> LOCATION: (1387)..(2298)
<220> FEATURE:
<221> NAME/KEY: CDS
<222> LOCATION: (2404)..(2640)
<220> FEATURE:
<221> NAME/KEY: CDS
<222> LOCATION: (2691)..(3257)
<220> FEATURE:
<221> NAME/KEY: CDS
<222> LOCATION: (3267)..(4079)
<220> FEATURE:
<221> NAME/KEY: CDS
<222> LOCATION: (4147)..(5784)
<220> FEATURE:
<221> NAME/KEY: CDS
<222> LOCATION: (5850)..(6830)
<220> FEATURE:
```

-continued

<221> NAME/KEY: CDS
<222> LOCATION: (6837)..(8279)
<220> FEATURE:
<221> NAME/KEY: CDS
<222> LOCATION: (8293)..(8661)

<400> SEQUENCE: 21

| | | | | |
|---|---|---|---|---|
| acctcgtatg | ggcagtaatt | cgccgtgtct | cccaaggtaa | gtctcccttt | gctgcagata | 60 |
| aggcgcacat | ccaccaccgg | ctgttgtctt | taggccatac | gcaccgccgc | accgtattgg | 120 |
| tgctctacct | gtgggtctcg | gctgttgcct | ttggcgcagt | tagctactcg | attgttccgc | 180 |
| cactgatcgc | aaccatcgca | acaattttgg | cgctggtggt | tgcaagtggc | gtgacactaa | 240 |
| ttccgttgcg | tcgtgggaaa | atcgacttcc | cagccaagcg | ttgacgtaga | caggcttttc | 300 |
| gatgatatcc | tgcgccacaa | gcgctactta | gagggttcaa | gttttcctta | cgtctgtagt | 360 |
| agagtgtccc | agcgtgagtg | atactttaaa | tggcgatggc | gccagcacca | gtagttttga | 420 |
| tgacccgcgc | gtgccactgc | agcgcgccct | gcggctgggc | tcgattgcgc | tagccataat | 480 |
| caccgtttta | tctctagcta | tctggggtgg | agttcgtggt | ctacccggaa | tctggggagt | 540 |
| agtcatcggc | gctgctattg | gcggtggctt | cgttctgatt | acggcagcgc | ttgtcctgtt | 600 |
| tactgcaaag | tctgcaccgt | ccaccaccat | ggctgttgtc | ctcggtggat | ggctactcaa | 660 |
| ggttgtactc | ttgattgtcg | tcctgatgat | cattcgggac | ctggaatttt | atgcacactat | 720 |
| ggctatgttc | atcacggttg | tcttggcgat | gattgcggta | ctcggtactg | aggtctgggg | 780 |
| aatcatcacc | tcccgcgtga | cttatatttc | ttaatagcta | ctagtgacat | gacgcccgct | 840 |
| ggggcgtcat | aggttgcgac | aaaggggagt | gcatctttag | ggatgtgctc | ccgtttgtga | 900 |
| tcgctaaacg | ggtggagtga | tggggtgtag | ggaaataggc | aaaacagtat | tttgatttat | 960 |
| ttgaattccc | tggtcgagac | atggcatgtg | acataaagca | tagaaaggca | aagggtgac | 1020 |
| gtatggcgaa | aaatgccttt | aacgtgcac | ctaaggggaa | ttgcaagggg | tgaaagcagg | 1080 |
| cagtgttatc | gggggtaatt | caaggggta | aaagactgtg | aaacggctat | tcaaaaaata | 1140 |
| actgtgatca | accttactaa | tgcctgtaaa | ccggggttgg | gctggggata | tgggctaatc | 1200 |
| caggggagc | aatcgcaggg | ttggctcaaa | cctcggaagt | tcggatgact | gcagatcgaa | 1260 |
| ataagcctca | atgagctgat | attatttcct | ccgggttacc | gcggaagcgg | cattagtaag | 1320 |
| attcgtgtcc | tgcgaaaaat | ttatgccgta | tcccatttac | ggtgattccc | tgttacagct | 1380 |
| tcgctgatgt | gcgacggagt | ccgtagctgt | gacagagagt | ttgagacgtc | catcgcaccg | 1440 |
| tacgacgtcg | acaatcgtac | ggcccgaaca | cgggagagaa | cgctgagcgt | tacaacattg | 1500 |
| gccatgaagg | gtagcttcca | cgcgcccgaa | ctggacccag | aatttttccc | ggggcaatat | 1560 |
| tacggcgaca | tcctgttcga | cgatgtgttg | ggcggatggt | tcgcacttga | tcgcatcatg | 1620 |
| ctggttcgtc | tgttgatgac | cgccgtcttg | gtgcttttat | ttattgcagc | atttaggaac | 1680 |
| ccaaagctgg | ttcctaaggg | actacagaac | gtcgcagaat | acgcgttaga | tttcgtccga | 1740 |
| attcacattg | ctgaggacat | cctgggcaag | aaggagggtc | gtcgcttcct | accgttgctg | 1800 |
| gcggctatct | tcttccggcac | ccttttctgg | aacgtctcca | cgattattcc | ggcactgaac | 1860 |
| atctccgcaa | acgctcgtat | tggcatgcct | attgtcttgg | ctggcgcagc | gtatatcgca | 1920 |
| atgatttacg | caggcaccaa | gcgctatggc | ttcgtaagt | acgtcaagtc | gtcgttggtt | 1980 |
| attcctaacc | ttccaccggc | tttgcacttg | ctggttgttc | caattgagtt | tttctcgacc | 2040 |
| ttcatccttgc | gtcccgtcac | tctggcaatt | cgtcttatgg | cgaacttcct | tgccggccac | 2100 |
| atcatttttgg | ttctgctgta | ctctgccacg | aacttcttct | tctggcagct | caacggctgg | 2160 |

```
acagcgatgt ccggtgtgac cctgctcgca gcggttctgt ttacggtcta cgagatcatc   2220
atcatcttcc tgcaggcata catctttgct ctgctgacgg cggtgtacat cgagttgtca   2280
cttcacgcag actcgcacta aggcgcgaac taaccggcct tgtaataacc cccactttaa   2340
gaccaactcc aacttcgctg aataaacga aaagcgaaga ttttcgaaa gggaacgact   2400
```
(partial — see below)

```
acagcgatgt ccggtgtgac cctgctcgca gcggttctgt ttacggtcta cgagatcatc   2220
atcatcttcc tgcaggcata catctttgct ctgctgacgg cggtgtacat cgagttgtca   2280
cttcacgcag actcgcacta aggcgcgaac taaccggcct tgtaataacc cccactttaa   2340
gaccaactcc aacttcgctg aataaacga  aaagcgaaga ttttttcgaaa gggaacgact   2400
ttcatgaacg acatcatctt ggctcaggca accgagacct ccttcgatgg ccttcagtcc   2460
atcggctacg gccttgcaac catcggccct ggcttgggta ttggtatcct cgtcggcaag   2520
accgttgagg gcatggcacg tcagcctgag atggctggcc agctgcgtac caccatgttc   2580
ctgggtatcg ccttcgttga ggctcttgca cttatcggcc tggttgcagg cttcctgttc   2640
taaaaagcgc gcgtttaaaa ccaaaccacc gtttttaaga ctggagactt atgaacaacg   2700
tcttttacta tcttgcagcg gaaggagagt cccttccact ggaaggtggc aactcccttc   2760
tgtttcccaa gagctatgac atcgtctggt ctctgatccc gttcttaatc atccttattg   2820
tcttcgcaat gtttgtcatt ccgaagttcc aggaactgtt gcaagagcgt gaagaccgga   2880
ttgagggcgg catcaagcgc gctgaagccc aacaggcaga agcaaaggcc gcacttgaga   2940
agtacaacgc acagctagct gacgctcgcg cagaggcagc tgaaatccgt gagcaggcgc   3000
gtgagcgcgg caagcagatt gaagcagagg caaagaccca ggcagaggaa gaagcacgcc   3060
gtatcgtcgc aggtggcgaa aaacagcttg aagcttcccg cgcacaggta gttgctgaac   3120
tgcgttccga tatcgacag  aactccatca acttggctga aagctgctc  ggcggtgaac   3180
tctctgagtc caccaagcag tcttcaacca ttgataactt cctgtccgag ctcgactctg   3240
tggcatcggc cggaaagtag gcaactatga aggcagctag ccgcgaatcg ctcgcatccg   3300
ctaccgagtc gctggattcc aatctggcag ctcaagcagg tgtagcagtg tccaccatga   3360
ccggcatgga actgttcgag gtttcccaag tattgggtga tgaccgcgaa ctccgtggag   3420
cagtcattga tgaatctgct tccactgaat cccgcaagaa gctcgttaat gatctcttcg   3480
gtgccaaagt ttctcctgct accttgcagg ttctggaaca gattgcatcg tcgaagtggt   3540
cgagcgcccg cgagatggtt tccggactga tcgctctttc acgtcgtgct ttgatgcgcg   3600
gcgcagaaag cgaaggacaa ctaggacagg tcgaagatga actcttccgc ttgtcccgga   3660
tcctggaccg cgaaggcgaa ctcacccagc tgctttctga ccgagctgca gaacctgcgc   3720
gtaagcgcaa gttgctggca gatgtgcttt acggaaaggt caccaaattc actgaggcgc   3780
ttgcgctgca ggtgattgac cgccctgagc acaatcccat tgatgacatt gcgaatctgg   3840
cggctgaagc agcacagctt cagggtcgca ctgttgcgca cgttgttagt gcgggtgaac   3900
tcaatgaagg ccagcaggca gtactcgccg agaagctggg caagatttat ggtcgtgcga   3960
tgtccatcca ctctgaggtt gacaccagcc tcctcggtgg tatgacaatc cgcgtaggcg   4020
atgaagttat tgacggttct accgcaggca aaattgagcg cctgcgtacc gctttgaagt   4080
agtcaactac aacgacagaa ttgatttaag taagtgctgg acgaatctac cgagagtagg   4140
aagaacatgg cggagctgac gatctcctcc gatgagatcc gtagcgcgat agcgaactac   4200
acctcgagct actccgcgga ggcctcccgt gaggaggtcg gcgtggtcat tcggcagct   4260
gacggtattg cacaggtttc tgggctacct tcagttatgg cgaatgagct gctcgagttc   4320
cctggcggcg taatcggcgt cgcacaaaac cttgaaacca actccattgg cgttgttatt   4380
cttggtaact acgagtccct caaagaaggc gaccaagtta agcgaactgg cgaagttctc   4440
tccatcccag tgggtgaaga gttcctcggc cgcgttatta acccattggg tcaggcaatt   4500
```

```
gacggcctgg gcccaatcgc tggcgaagag gaccgcgtcc tcgagctgca ggcaccttcc   4560
gtgttgcagc gtcagccagt tgaagagcca atgcagaccg gcatcaaggc tattgatgct   4620
atgaccccaa tcggtcgcgg tcagcgtcag ctcatcattg gtgaccgtaa gactggtaaa   4680
accgcagtct gcatcgacac catccttaac cagaaggcta actgggaatc cggcgacaag   4740
aacaagcaag ttcgttgtat ctacgtcgct attggtcaga agggctccac catcgctggt   4800
gtccgcaaga ccctcgaaga gcaggcgct ctggagtaca ccaccatcgt ggctgctcct   4860
gcttctgact ccgcgggctt caagtggttg gcaccattct ccggtgctgc tcttggtcag   4920
cactggatgt accagggcaa ccacgtcttg gtcatctatg atgacttgac caagcaggct   4980
gaggcttacc gtgcgatttc cctgttgctg cgtcgcccgc cgggccgcga agcttaccca   5040
ggtgacgtct tctacttgca ctcccgtctg ctggagcgtg ctgcgaagct ctccgatgat   5100
ttgggtgcag gttctttgac cgcactgcca attattgaaa ccaaggcgaa tgacgtgtct   5160
gcgttcattc caaccaacgt tatttccatt accgacggcc aggtcttcct ggagtccgac   5220
ctgttcaacc aaggcgtccg tccggcaatt aacgtcggtg tgtcggtttc ccgtgttggt   5280
ggcgctgctc agaccaaggg tatgaagaag gttgcaggta acctgcgtct tgacctcgct   5340
tcctaccgtg atctgcaggg cttttgctgcc ttcgcttctg acttggaccc agtgtccaag   5400
gcccagcttg agcgcggtga gcgtctggtt gagatcctga agcagtctga gtcttctcct   5460
caggcagtcg agtaccagat ggtttccatc ttcttggctg aagaaggcgt cttcgacgtc   5520
gttcctgtcg aagatgttcg tcgctttgag gctgacgttc aggaatacct gcagcagaac   5580
accccagagg tttacgagca gattgccggc ggtaaggcat ttaccgacga gtccaaggaa   5640
gccctgttgg ctgcagctaa ggacttcact ccttccttcc gcaccaccga gggccacaac   5700
ttgggcactg aagctccagt tgatccttg gctgaagaag aagtcaagaa gactgaagtc   5760
accgtctccc gtaagtcggc taagtaaaga cctccgggta cttactcaca ctgactgaat   5820
agaaatttag aagggaggag cgaaacaaca tggcaaatct tcgcgaattg cgcgaccgta   5880
tccggtccgt gaactcgacc aagaagatca ccaaggcgca ggagctgatt gcaacttctc   5940
gcattaccaa ggcgcaagcc aaggttgatg cagcagcacc gtacgcacac gagatgtcga   6000
acatgatgga ccgtcttgca tcggctagct cgttggagca cccaatgctg cgccaccgtg   6060
aaaacggcaa agttgcagcc gtactcgtgg tctcttctga ccgcggtatg tgtggtggct   6120
acaacaacaa cgtctcttaag aaggctgctg agctcgaagg actccttcgc ggtcaaggct   6180
tcgacgttgt ccgctacgta accggtagca agggcgtcgg ctactacaac ttccgtgaga   6240
aggaagttgt gggcgcgtgg actggctttt ctcaggatcc gtcctgggaa ggcactcacg   6300
acgttcgtca ccacttggtt gacggcttca ttgctggctc cgaaggtaca actccggccc   6360
gtcagggcgt gaacaccgaa gaccaaacgg tacgtggttt cgaccaggta cacgttgttt   6420
acaccgagtt cgaatccatg ctggttcaga ctccacgtgc tcaccagttg ttgccgattg   6480
aaccggtaat taagaagag gaacttcacc tgggcgactc ggcgctagaa gccaaccctg   6540
atgctcaggg cctgtctgct gactacgagt ttgagccgga tgcagatact ttgctctcgg   6600
cacttctgcc gcagtatgta tcacgtatcc ttttctcgat gttcttggag gcttcggctt   6660
ctgagtccgc agctcgtcga actgcaatga aggctgcgac tgacaacgct aatgacttgg   6720
taaccgactt gtctcgtgtt gctaaccagg ctcgtcaggc gcagattacc caggaaatca   6780
cagaaatcgt cggtggcgct ggcgcgctcg ccgaaagcgc agaaagtgac tagattatga   6840
ctacagctct gcatgagcag aacacacagg agtcggcaat tgccggccgt gtggtgcgtg   6900
```

-continued

```
tcatcggtcc ggtcgtcgac gtggagttcc cgcgtggcgg actaccggca ctgtataatg    6960
cactgaccgt cgagattaac ctcgagtctg ttgcacgcac cattacccct gaggttgcac    7020
agcacctcgg cgacaacctg gttcgtaccg tttcgatggc acctaccgat ggtcttgttc    7080
ggcgtgcggc agtaaccgat accgaggcac caatctccgt gccagttggc gatgttgtta    7140
agggccacgt ctttaacgca ttgggcgact gcttggatga ccaggtctg ggccgcgatg     7200
gcgagcagtg gggcatccac cgcgagccac cagcattcga ccagctcgaa ggcaagaccg    7260
agatcctcga aaccggcatt aaggtcatcg accttttgac cccatacgtc aagggcggca    7320
agattggcct cttcggcggt gcgggtgttg gtaagaccgt tctgattcag gaaatgatta    7380
ctcgtatcgc acgcgagttc tctggtacct ccgtgttcgc tggtgttggc gagcgtaccc    7440
gtgagggcac cgacctgttc ttggaaatgg aagaaatggg cgtactgcag gacaccgccc    7500
tcgtgttcgg ccagatggac gaaccgccag gagttcgtat gcgcgtagct ctgtccggtc    7560
tgaccatggc ggagtacttc cgcgatgttc agaaccagga cgtgctgctg ttcatcgata    7620
acatcttccg tttcactcag gctggttctg aagtttcgac ccttctgggc cgtatgcctt    7680
ccgctgtggg ctaccagcca accttggctg atgagatggg tgtactccag gagcgcatta    7740
cctctactaa gggtaagtcg attacctctc tgcaggccgt ttacgttcct gccgatgact    7800
acactgaccc agctccagcg accaccttcg ctcacttgga tgcaaccacc gagcttgacc    7860
gtgcgattgc ttccaagggt atctacccag cagtgaaccc actgtcgtcg acttctcgta    7920
ttctcgagcc aagcatcgtc ggtgagcgtc actacgctgt tgctcagcgc gtgatcaaca    7980
ttttgcagaa gaacaaggaa ctgcaggata ttatcgcgat tctgggtatg gacgagctgt    8040
ctgaagagga caagatcacc gttcagcgcg cacgtcgcat tgagcgcttc ttgggccaga    8100
acttcttcgt cgcagagaag ttcaccggcc tgccaggctc ttacgtacct ttggcagata    8160
ccatcgacgc tttcgagcgc atttgcaacg gcgaattcga ccactaccca gagcaggcct    8220
tcaacggctt gggtggcttg gacgacgtcg aagcagcgta caagaagctg actgagaagt    8280
agggagaggc acatgctga catcaccgtg gaactggttt ctgttgagcg catgctgtgg    8340
tctggaaagg ccaccatcat ttccgcagag accaccgagg gtgagatcgg cgtgcttccg    8400
ggtcacgaac cattgcttgg ccagctggct gagaatggcg tagttacctt ccgtcctgtc    8460
gacggtgacc gcaaggtcgc cgctgttcag ggtggcttcc tctccgtatc caccgagaag    8520
atcaccgtct ggcggactg ggcagttttgg gcagatgagg ttaatgaatc tcaggctcaa    8580
gaagatgcct tgtcttccga tgaattggtt tcttctcgtg gacaggcagc gcttcgcgcc    8640
ttggctcgtt cccgcgaaag ctaatccttt caaagactcg ttctttctaa aggttgctta    8700
agcaccgagg attcggagat ttagggcagc aatgaccgcc cttcctctct cataaagaac    8760
ccgcagtaat aattgctgcg ggttcttttt tgccgtttta gccagcttgt gtgcgaagac    8820
tatcgctgta gcccgagcgg ggcctacagc agaggtctgg gcggaggtag tcaaccaaac    8880
gatttattgt gactctatgc aggcgctctg tagactattc aacaacttga gattgattga    8940
accgcttcta ggcagtttgg ttgaggcagt tcagataagg tgttctgcct cgcccgtgcc    9000
atgagcggtt gtgacggaga agggaagagc gggactgatg agcgtggttt cggtaatcct    9060
ttggttgctc gccattattg ccatactatg tattttcttc gcagcgatgc gcttttttcac   9120
cttgcggtca cgcggtgctt cagtgttgat gcgcaagctc ccggccaagg gctaccacgg    9180
ctggcgccat ggtgtgctgc gctacaaggg agacactgta gatttctaca agcttcgctc    9240
```

-continued

| | | | | |
|---|---|---|---|---|
| cgtgtggcct | atggccgatc | actcatttag | tcgcctcgac | atcgagttgc tggattctcg 9300 |
| tcccgcaact | gatggcgagg | ctgctttcat | ttccaaggac | tatttgatct tctgcttcag 9360 |
| cgcagctggc | aagggctacg | agctcgcgtg | tacgcagcac | gccatgatgg catttggcgc 9420 |
| gtgggtggaa | gcctcgccgt | cgcagcgtaa | ggaacagatt | gattttcgtc gtttgcgcga 9480 |
| acgggcaacg | cgtccgcggg | | | 9500 |

US 7,223,581 B2

$F_0F_1$-ATPASE AND DNA ENCODING THE SAME

This application is a Divisional Application of application Ser. No. 09/901,884, filed Jul. 9, 2001 now abandoned.

BACKGROUND OF THE INVENTION

The present invention relates to a novel $F_0F_1$-ATPase, a DNA encoding the $F_0F_1$-ATPase, a method for producing the $F_0F_1$-ATPase, and a method for producing nucleoside 5'-triphosphate; using the $F_0F_1$-ATPase.

$F_0F_1$-ATPase plays principal roles in the biological energy metabolism, because the enzyme has an activity of generating adenosine 5'-triphosphate (ATP) as an energy source of organisms, by utilizing the gradient of proton concentration between the intramembrane and the extramembrane. Therefore, utilization of $F_0F_1$-ATPase enables us to develop a living thing with improved energy metabolism.

Herein, $F_0F_1$-ATPase is synonymous with $H^+$-ATPase.

Because it has been known that the activity of $F_0F_1$-ATPase varies, depending on the change of outer environment, such as pH, the utilization of $F_0F_1$-ATPase can provide a living thing adaptable to the change of outer environment [Mol. Microbiol., 33, 1152 (1999), J. Bacteriol., 176, 5167 (1994)].

$F_0F_1$-ATPase is a protein complex comprising a soluble catalytic sector $F_1$ and a transmembrane sector $F_0$ functioning as proton channel. In organisms such as Escherichia coli and Bacillus subtilis, $F_1$ is composed of five subunits of α, β, γ, δ and ε, while $F_0$ is composed of three subunits of a, b and c [Annu. Rev. Biochem., 66, 717 (1997)].

Concerning the $F_0F_1$-ATPase gene, the gene was isolated from Escherichia coli [Biochem. J., 224, 799 (1984)], Bacillus subtilis [J. Bacteriol., 176, 6802 (1994)], Bacillus megaterium [J. Biol. Chem., 264, 1528 (1989)], Bacillus firmus [Mol. Gen. Genet., 229, 292 (1991)], Bacillus sp. PS3 [Biochim. Biophys. Acta,. 933, 141 (1988)], Methanosarcina barkeri [Biochem. Biophys. Res. Commun., 241, 427 (1997)], Lactobacillus acidophilus [Mol. Microbiol., 33, 1152 (1999)], Rhodobacter capsulatus [J. Bacteriol., 180, 416 (1998), Arch. Microbiol., 170, 385 (1998)] and the like, but no gene derived from microorganisms belonging to the genus Corynebacterium has been isolated yet.

Regarding the production of nucleoside 5'-triphosphate, methods using microorganisms (Japanese Published Unexamined Patent Application No.107593/1979; Japanese Published Unexamined Patent Application No. 51799/1984; J. Ferment. Bioeng., 68, 417 (1989)) and a method using enzymes (WO 98/22614) have been known. However, the productivity of nucleoside 5'-triphosphate is insufficient.

SUMMARY OF THE INVENTION

It is the purpose of the present invention to provide a protein complex having the $F_0F_1$-ATPase activity; a DNA encoding the protein complex; a method for producing the protein complex having the $F_0F_1$-ATPase activity, using the DNA; and a method for producing nucleoside 5'-triphosphate, using the protein complex.

For this purpose, the present inventors have made various investigations. Consequently, the inventors have successfully isolated the genes encoding component proteins of which a protein complex having the $F_0F_1$-ATPase activity is composed, from Corynebacterium ammoniagenes. Thus, the present invention has been accomplished.

The present invention relates to the following (1) to (32) subject matters.

(1) A protein selected from the group consisting of the following proteins (a) to (c):
(a) a protein having the amino acid sequence represented by SEQ ID NO: 1;
(b) a protein having a modified one of the amino acid sequence represented by SEQ ID NO: 1, where one or more amino acids are deleted, substituted or added, and exerting the $F_0F_1$-ATPase activity when the protein forms a complex with all the individual proteins having the amino acid, sequences represented by each of SEQ ID NOS: 2 to 8; and
(c) a protein having an amino acid sequence having 70% or more identical to the amino acid sequence represented by SEQ ID NO: 1 and exerting the $F_0F_1$-ATPase activity when the protein forms a complex with all the individual proteins having the amino acid sequences represented by each of SEQ ID NOS: 2 to 8.

(2) A protein selected from the group consisting of the following proteins (a) to (c):
(a) a protein having the amino acid sequence represented by SEQ ID NO: 2;
(b) a protein having a modified one of the amino acid sequence represented by SEQ ID NO: 2, where one or more amino acids are deleted, substituted or added, and exerting the $F_0F_1$-ATPase activity when the protein forms a complex with all the individual proteins having the amino acid sequences represented by each of SEQ ID NO: 1 and SEQ ID NO: 3 to 8; and
(c) a protein having an amino acid sequence having 70% or more identical to the amino acid sequence represented by. SEQ ID NO: 2 and exerting the $F_0F_1$-ATPase activity when the protein forms a complex with all the individual proteins having the amino acid sequences represented by each of SEQ ID NO: 1 and SEQ ID NOS: 3 to 8.

(3) A protein selected from the group consisting of the following proteins (a) to (c):
(a) a protein having the amino acid sequence represented by SEQ ID NO: 3;
(b) a protein having a modified one of the amino acid sequence represented by SEQ ID NO: 3, where one or more amino acids are deleted, substituted or added, and exerting the $F_0F_1$-ATPase activity when the protein forms a complex with all the proteins having the individual amino acid sequences represented by each of SEQ ID NOS: 1 and 2 and SEQ ID NOS: 4 to 8; and
(c) a protein having an amino acid sequence having 70% or more identical to the amino acid sequence represented by SEQ ID NO: 3 and exerting the $F_0F_1$-ATPase activity when the protein forms a complex with all the individual proteins having the amino acid sequences represented by each of SEQ ID NOS: 1 and 2 and SEQ ID NOS: 4 to 8.

(4) A protein selected from the group consisting of the following proteins (a) to (c):
(a) a protein having the amino acid sequence represented by SEQ ID NO: 4;
(b) a protein having a modified one of the amino acid sequence represented by SEQ ID NO: 4, where one or more amino acids are deleted, substituted or added, and exerting the $F_0F_1$-ATPase activity when the protein forms a complex with all the individual proteins having the amino acid sequences represented by each of SEQ ID NOS: 1 to 3 and SEQ ID NOS: 5 to 8; and
(c) a protein having an amino acid sequence having 70% or more identical to the amino acid sequence represented by SEQ ID NO: 4 and exerting the $F_0F_1$-ATPase activity when the protein forms a complex with all the individual proteins having the amino acid sequences represented by each of SEQ ID NO: 1 to 3 and SEQ ID NOS: 5 to 8.

(5) A protein selected from the group consisting of the following proteins (a) to (c):
(a) a protein having the amino acid sequence represented by SEQ ID NO: 5;
(b) a protein comprising a modified one of the amino acid sequence represented by SEQ ID NO: 5, where one or more amino acids are deleted, substituted or added, and exerting the $F_0F_1$-ATPase activity when the protein forms a complex with all the individual proteins having the amino acid sequences represented by each of SEQ ID NOS: 1 to 4 and SEQ ID NOS: 6 to 8; and
(c) a protein having an amino acid sequence having 70% or more identical to the amino acid sequence represented by SEQ ID NO: 5 and exerting the $F_0F_1$-ATPase activity when the protein, forms a complex with all the individual proteins having the amino acid sequences represented by each of SEQ ID NOS: 1 to 4 and SEQ ID NOS: 6 to 8.

(6) A protein selected from the group consisting of the following proteins (a) to (c):
(a) a protein having the amino acid sequence represented by SEQ ID NO: 6;
(b) a protein having a modified one of the amino acid sequence represented by SEQ ID NO: 6, where one or more amino acids are deleted, substituted or added, and which can exert the $F_0F_1$-ATPase activity when the protein forms a complex with all the individual proteins having the amino acid sequences represented by each of SEQ ID NOS: 1 to 5 and SEQ ID NOS: 7 and 8; and
(c) a protein having an amino acid sequence having 70% or more identical to the amino acid sequence represented by SEQ ID NO: 6 and exerting the $F_0F_1$-ATPase activity when the protein forms a complex with all the individual proteins having the amino acid sequences represented by each of SEQ ID NOS: 1 to 5 and SEQ ID NOS: 7 and 8.

(7) A protein selected from the group consisting of the following proteins(a) to (c):
(a) a protein having the amino. acid sequence represented by SEQ ID NO: 7;
(b) a protein having a modified one of the amino acid sequence represented by SEQ.ID NO: 7, where one or more amino acids are deleted, substituted or added, and exerting the $F_0F_1$-ATPase activity when the protein forms a complex with all the individual proteins having the amino acid sequences represented by each of SEQ ID NOS: 1 to 6 and SEQ ID NO: 8; and
(c) a protein having an amino acid sequence having 70% or more identical to the amino acid sequence represented by SEQ ID NO: 7 and exerting the $F_0F_1$-ATPase activity when the protein forms a complex with all the individual proteins having the amino acid sequences represented by each of SEQ ID NOS: 1 to 6 and SEQ ID NO: 8.

(8) A protein selected from the group consisting of the following proteins (a) to (c):
(a) a protein having the amino acid sequence represented by SEQ ID NO: 8;
(b) a protein having a modified one of the amino acid sequence represented by SEQ ID NO: 8, where one or more amino acids are deleted, substituted or added, and exerting the $F_0F_1$-ATPase activity when the protein forms a complex with all the individual proteins having the amino acid sequences represented by each of SEQ ID NOS: 1 to 7; and
(c) a protein having an amino -acid sequence having 70% or more identical to the amino acid sequence represented by SEQ ID NO: 8 and exerting the $F_0F_1$-ATPase activity when the protein forms a complex with all the individual proteins comprising the amino acid sequences represented by each of SEQ ID NOS: 1 to 7.

(9) A protein complex comprising eight proteins respectively selected from the eight groups as defined by each of (1) to (8).

(10) A DNA encoding any one of the proteins of (1) to (8).

(11) A DNA selected from the group consisting of the following DNAs (a) and (b):
(a) a DNA having the nucleotide sequence represented by SEQ ID NO:9; and
(b) a DNA hybridizing with the DNA under stringent conditions and encoding a protein exerting the $F_0F_1$-ATPase activity when the protein forms a complex with all the individual proteins having the amino acid sequences represented by each of SEQ ID NOS: 2 to 8.

(12) A DNA selected from the group consisting of the following DNAs (a) and (b):
(a) a DNA having the nucleotide sequence represented by SEQ ID NO: 10; and
(b) a DNA hybridizing with the DNA under stringent conditions and encoding a protein exerting the $F_0F_1$-ATPase activity when the protein forms a complex with all the individual proteins having the amino acid sequences represented by each of SEQ ID NO: 1 and SEQ ID NOS: 3 to 8.

(13) A DNA selected from the group consisting of the following DNAs (a,) and (b):
(a) a DNA having the nucleotide sequence represented by SEQ ID NO: 11; and
(b) a DNA hybridizing with the DNA under stringent conditions and encoding a protein exerting the $F_0F_1$-ATPase activity when the protein forms a complex with all the individual proteins having the amino acid sequences represented by each of SEQ ID NOS: 1 and 2 and SEQ ID NOS: 4 to 8.

(14) A DNA selected from the group consisting of the following DNAs (a) and (b):
(a) a DNA having the nucleotide sequence represented by SEQ ID NO:12; and
(b) a DNA hybridizing with the DNA under stringent conditions and encoding a protein exerting the $F_0F_1$-ATPase activity when the protein forms a complex with all the individual proteins having the individual amino acid sequences represented by each of SEQ ID NOS: 1 to 3 and SEQ ID NOS: 5 to 8.

(15) A DNA selected from the group consisting of the following DNAs (a) and (b):
(a) a DNA having the nucleotide sequence represented by SEQ ID NO:13; and
(b) a DNA hybridizing with the DNA under stringent conditions and encoding a protein exerting the $F_0F_1$-ATPase activity when the protein forms a complex with all the individual proteins having the amino acid sequences represented by each of SEQ ID NOS: 1 to 4 and SEQ ID NOS: 6 to 8.

(16) A DNA selected from the group consisting of the following DNAs (a) and (b):
(a) a DNA having the nucleotide sequence represented by SEQ ID NO: 14; and
(b) a DNA hybridizing with the DNA under stringent conditions and encoding a protein exerting the $F_0F_1$-ATPase activity when the protein forms a complex with all the individual proteins having the amino acid sequences represented by each of SEQ ID NOS: 1 to 5 and SEQ ID NOS: 7 and 8.

(17) A DNA selected from the group consisting of the following DNAs (a) and (b):
(a) a DNA having the nucleotide sequence represented by SEQ ID NO: 15; and
(b) a DNA hybridizing with the DNA under stringent conditions and encoding a protein exerting the $F_0F_1$-ATPase activity when the protein forms a complex with all the individual proteins having the amino acid sequences represented by each of SEQ ID NOS: 1 to 6 and SEQ ID NO: 8.
(18) A DNA selected from the group consisting of the following DNAs (a) and (b):
(a) a DNA having the nucleotide sequence represented by SEQ ID NO: 16; and
(b) a DNA hybridizing with the DNA under stringent conditions and encoding a protein exerting the $F_0F_1$-ATPase activity when the protein forms a complex with all the individual proteins having the amino acid sequences represented by each of SEQ ID NOS: 1 to 7.
(19) A DNA comprising the eight DNAs respectively selected from the eight groups as defined by each of (11) to (18).
(20) A DNA having the nucleotide sequences represented by SEQ ID NOS: 9 to 16.
(21) A DNA having the nucleotide sequence represented by SEQ ID NO: 21.
(22) The DNA according to any one of (10) to (21), where the DNA is derived from a microorganism belonging to the genus *Corynebacterium*.
(23) The DNA according to any one of (10) to (21), where the DNA is derived from a microorganism of the species *Corynebacterium ammoniagenes*.
(24) A recombinant DNA constructed by inserting the DNA according to any one of (10) to (18) into a vector.
(25) A recombinant DNA constructed by inserting the DNA according to any one of (19) to (21) into a vector.
(26) A transformant obtained by transformation of a host cell with the recombinant DNA of (24) or (25).
(27) A transformant of (26), where the host cell is a microorganism of the species *Escherichia coli*, *Corynebacterium glutamicum* or *Corynebacterium ammoniagenes*.
(28) A method for producing a protein of any one of (1) to (8), which comprises culturing a transformant obtained by transformation of a host cell with the recombinant DNA of (24) in a culture medium, so as to allow the protein of any one of (1) to (8) to be expressed and accumulated in the culture and harvesting the protein from the culture.
(29) A method for producing a protein complex having the $F_0F_1$-ATPase activity, which comprises culturing a transformant obtained by transformation of a host cell with the recombinant DNA of (25) in a culture medium, so as to allow a protein complex having the $F_0F_1$-ATPase activity to be expressed and accumulated in the culture and recovering the protein complex from the culture.
(30) A method for producing nucleoside 5'-triphosphate, which comprises by use of a culture of a transformant obtained by transformation of a host cell with the recombinant DNA of (25) or a treated product of the culture as an enzyme source, allowing the enzyme source and a precursor of nucleoside 5'-triphosphate to co-exist with each other in an aqueous medium to generate and accumulate the nucleoside 5'-triphosphate and recovering the nucleoside 5'-triphosphate from the aqueous medium.
(31) The method of (30), where the precursor of nucleoside 5'-triphosphate is adenine, guanine, uracil, cytosine, hypoxanthine, adenosine, guanosine, uridine, cytidine, inosine, adenosine 5'-monophosphate, guanosine 5'-monophosphate, uridine 5'-monophosphate, cytidine 5'-monophosphate or inosine 5'-monophosphate.
(32) The method of (30), where the nucleoside 5'-triphosphate is adenosine 5'-triphosphate, guanosine 5'-triphosphate, uridine 5'-triphosphate or cytidine 5'-triphosphate.

Figure 1:
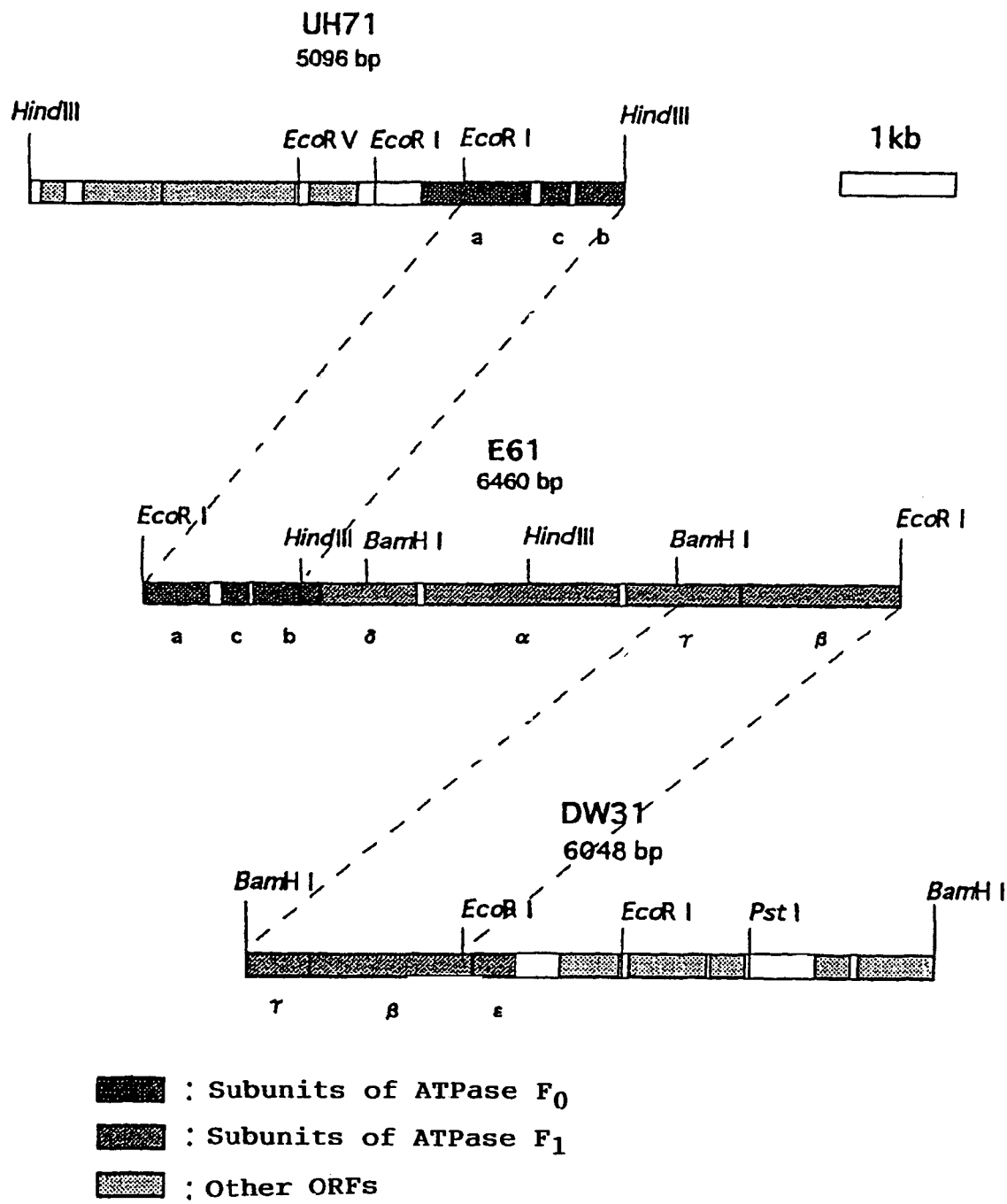
FIG. 1 shows restriction maps of fragments inserted in plasmids pUH71, pE61 and pDW31 and the open reading frames contained in the fragments.

DETAILED DESCRIPTION OF THE INVENTION (1) Preparation of the DNA of the Present Invention (a) Preparation of a DNA Library The protein complex of the present invention is a protein complex comprising the individual proteins having the amino acid sequences represented by each of SEQ ID NOS: 1 to 8 as components.

As long as the protein complex exerts the $F_0F_1$-ATPase activity, one or more amino acids can be deleted, substituted or added in the amino acid sequences of the individual proteins.

The protein having an amino acid sequence with one or more amino acids deleted, substitutied or added, which can be the component of the protein complex having the $F_0F_1$-ATPase activity, can be obtained by introducing.mutation in the DNA encoding the protein having any one of SEQ ID NOS: 1 to 8, via the site-directed mutagenesis described in Molecular Cloning, A Laboratory Manual, Second Edition, Cold Spring Harbor Laboratory Press (1989) (abbreviated as Molecular Cloning, Second edition, hereinafter), Current Protocols in Molecular Biology, John Wiley & Sons (1987–1997) (abbreviated Current Protocols in Molecular Biology, hereinafter), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985), and the like.

The number of the amino acids to be deleted, substituted, or added is not particularly limited, but should be such that deletion, substitution or addition according to well-known methods such as site-directed mutagenesis can be ocurred. The number is one to several tens, preferably one to 20, more preferably one to 10, still more preferably one to 5.

In order for the protein complex according to the present invention to have the $F_0F_1$-ATPase activity, each component protein of the protein complex has such identity to the corresponding amino acid sequences represented by each of SEQ ID NOS: 1 to 8, as at least 60%, preferably 80% or more, more preferably 95% or more. The identity of a nucleotide sequence or an amino acid sequence can be determined using the algorithm "BLAST" by Karlin and Altschl [Proc. Natl. Acad. Sci. USA, 90, 5873–5877 (1993)]. The programs called "BLASTN" and "BLASTX" have been developed based on the above algorithm [J. Mol. Biol., 215 403–410 (1990)]. In the case of analyzing a nucleotide sequence based on BLAST, the parameter can be set to e.g. score=100, wordlength=12. In the case of analyzing an amino acid sequence based on BLASTX, the parameter can be set to e.g. score=50, wordlength=3. In the case of using BLAST or Gapped BLAST program, a default parameter of each program can be used. The specific analysis methods of using the above programs are known in the art (see www.ncbi.nlm.nih.gov).

However, the protein of the present invention does not include any proteins having the amino acid sequences in the public domain.

The DNAs of the present invention encode the proteins of the present invention or the protein complex comprising the proteins as the components and can be isolated from a microorganism of the genus *Corynebacterium*. The microorganism belonging to the genus *Corynebacterium* includes, for example, *Corynebacterium ammoniagenes*, specifically *Corynebacterium ammoniagenes* strain ATCC6872. Specific examples of the DNA of the present invention include DNAs having the nucleotide sequence represented by any one of SEQ ID NOS: 9 to 16, a DNA comprising all the individual nucleotide sequences, and a DNA having the nucleotide sequence represented by SEQ ID NO: 21.

Additionally, DNAs hybridizing under stringent conditions with the DNA having the nucleotide sequence represented by any one of SEQ ID NOS: 9 to 16, a DNA comprising all the individual nucleotide sequences, and a DNA represented by the nucleotide sequence represented by SEQ ID NO: 21 are also encompassed within the scope of the DNA of the present invention. The DNA hybridizing under stringent conditions can be isolated by colony hybridization, plaque hybridization or Southern hybridization or the like, using the DNAs of the nucleotide sequences represented by any one of SEQ ID NOS: 9 to 16, the DNA comprising all the individual nucleotide sequences or the DNA of the nucleotide sequence represented by SEQ ID NO: 21 as the probe. Specifically, the DNA includes a DNA isolated and identified by using a filter on which the colony or plaque-derived DNA is immobilized, for hybridization in the presence of 0.7 to 1.0 mol/liter NaCl at 65° C. and subsequent washing of the filter with 0.1× to 2×SSC (saline-sodium citrate) solution [1×SSC solution (150 mmol/liter NaCl, 15 mmol/liter sodium citrate); n×means solution at n–fold concentration] under a condition of 65° C.

The hybridization can be promoted according to the method described in experimental text books, such as Molecular Cloning, Second edition; and Current Protocols in Molecular Biology, DNA Cloning 1: Core Techniques, A Practical Approach, Second Edition, Oxford University (1995). Specifically, the hybridizable DNA includes DNA with at least 80%, preferably 95% or more identical to the DNA of the nucleotide sequence represented by any one of the nucleotide sequences of SEQ ID NOS: 9 to 16, the DNA comprising all the individual nucleotide sequences, or the DNA of the nucleotide sequence represented by SEQ ID NO: 21, when the identity is calculated by BLAST and the like as described above.

However, the DNA of the present invention does not include DNAs in the public domain.

The method for isolating the DNA of the present invention is described hereinbelow.

A microorganism belonging to the genus *Corynebacterium* is cultured according to a known method [for example, Appl. Microbiol. Biotechnol., 39, 318 (1993)]. After culturing, the chromosomal DNA of the microorganism is isolated and purified according to a known method [for example, Current Protocols in Molecular Biology, Agric. Biol. Chem., 49, 2925 (1985)].

A method for preparing a DNA library includes methods described in, for example, Molecular Cloning, Second edition; and Current Protocols in Molecular Biology, DNA Cloning 1: Core Techniques, A Practical Approach Second Edition, Oxford University Press (1995).

As the cloning vector for preparing the DNA library, any cloning vector autonomously replicable in *Escherichia coli* strain K12 can be used, including phage vector and plasmid vector. Specifically, the cloning vector includes ZAP Express [manufactured by stratagene, Strategies, 5, 58 (1992)], λzap II (manufactured by Staratagene), λgt10 and λgt11 [DNA Cloning, A Practical Approach, 1, 49 (1985)], λTriplEx (manufactured by Clontech), λExCell (manufactured by Amersham Pharmacia Biotech), pBluescript II KS (−) and pBluescript II SK (+) [manufactured by Stratagene, Nucleic Acids Research, 17, 9494 (1989)], pUC18 [Gene, 33, 103 (1985)] and the like.

As the *Escherichia coli* for transformation with the vector in which the DNA is inserted, any microorganism belonging to the species *Escherichia coli* can be used. Specifically, the microorganism includes *Escherichia coli* XL1-Blue MRF' [manufactured by Stratagene, Strategies, 5, 81 (1992)], *Escherichia coli* C600 [Genetics, 39, 440 (1954)], *Escherichia coli* Y1088 [Science, 222, 778 (1983)], *Escherichia coli* Y1090 [Science, 222, 778 (1983)], *Escherichia coli* NM522 [J. Mol. Biol., 166, 1 (1983)], *Escherichia coli* K802 [J. Mol. Biol., 16, 118 (1966)], *Escherichia coli* JM109 [Gene, 33, 103 (1985)] and the like.

(b) Acquisition of the DNA of the Present Invention

The objective clone can be selected from the DNA library by colony hybridization, plaque hybridization or Southern hybridization, as described in experimental textbooks such as Molecular Cloning, Second edition; and Current Protocols in Molecular Biology, DNA Cloning 1: Core Techniques, A Practical Approach, Second Edition, Oxford University (1995).

The DNA probe for use in the hybridization includes, for example, DNA isolated by PCR [PCR Protocols, Academic Press (1990)] using DNA primers designed from known sequences, in addition to known genes or parts of the known genes and DNA synthesized on the basis of known sequences. The DNA probe includes, for example, a DNA fragment isolated from *Escherichia coli* chromosome by using the synthetic DNAs of SEQ ID NOS: 17 and 18 as primers, designed on the basis of the sequence of $F_0F_1$-ATPase β subunit gene of *Escherichia coli*.

The isolated DNA as it is or after cleavage with an appropriate restriction endonuclease is inserted into a vector. Then, the nucleotide sequence of the DNA is determined by methods for nucleotide sequencing for general use, for example the dideoxy method [Proc. Natl. Acad. Sci. USA, 74, 5463 (1977)] using 373A ·DNA sequencer (manufactured by Perkin Elmer).

In case that the resulting DNA contains only a part of the DNA of the present invention, the full-length DNA can be isolated by hybridization with a DNA fragment as probe, isolated by PCR using primers designed from the isolated DNA sequence.

The vector in which the isolated DNA of the present invention is inserted includes pBluescript KS (−) (manufactured by Stratagene), pDIRECT [Nucleic Acids Research, 18, 6069(1990)], pCR-ScriptAmp SK (+) (manufactured by Staratagene), pT7Blue (manufactured by Novagen), pCR II (manufactured by Invitrogen Corporation), pCR-TRAP (manufactured by Gene Hunter) and pNoTAT7 (manufactured by 5 Prime→3 Prime Co.).

The DNA having the novel nucleotide sequence isolated as described above includes, for example, the DNA having the nucleotide sequence represented by SEQ ID NO: 21.

The DNA having the nucleotide sequence represented by SEQ ID NO: 21 encodes all the individual proteins having the amino acid sequences represented by each of SEQ ID NOS: 1 to 8.

The bacterial strain carrying a plasmid comprising the DNA having the nucleotide sequence represented by SEQ ID NO: 21 includes, for example, *Escherichia coli* JM109/pE61, JM109/pDW31 and JM109/pUH71.

Further, the objective DNA can be isolated by preparing primers based on the nucleotide sequence thus determined and carrying out PCR using the chromosomal DNA as the template and the primers.

The DNA encoding any one of the component proteins of the protein complex of the present invention can be obtained by cleaving the DNA obtained above with a restriction endonuclease and the like.

For example, the DNA encoding any one of the proteins of SEQ ID NOS: 1 to 8 can be isolated as the DNA having any one of the nucleotide sequences repersented by SEQ ID NOS: 9 to 16, respectively, by cleaving the DNA of SEQ ID NO: 21 and individually isolating the resulting DNA.

Based on the thus determined nucleotide sequence of DNA, furthermore, the objective DNA can be prepared by chemical synthesis by means of DNA synthesizers such as the DNA synthesizer of Model 8905, manufactured by Perceptive Biosystems, Co.

[2] Production of the Proteins and the Protein Complex of the Present Invention

The proteins and the protein complex of the present invention can be prepared, for example, by expressing the DNA of the present invention in a host cell by the following procedures according to the method described in Molecular Cloning, Second edition, Current Protocols in Molecular Biology and the like.

More specifically, a recombinant DNA is prepared by inserting the DNA of the present invention downstream the promoter of an appropriate expression vector, which is then used for transformation of a host cell compatible with the expression vector, so that a transformant in which the protein or protein complex of the present invention is expressed can be obtained. As the host cell, any host cell capable of having the objective gene expressed, such as bacteria, yeast, an animal cell, an insect cell and a plant cell, can be used. As the expression vector, a vector having autonomous replication in the host cell or integration into the chromosome of the host cell and containing a promoter at a position where the DNA encoding the protein or protein complex of the present invention can be transcribed, is used.

In case that prokaryotic organisms such as bacteria are used as host cells, it is preferred that the recombinant DNA containing the DNA encoding the protein or protein complex of the present invention can autonomously replicate in the bacteria and simultaneously that, the recombinant DNA is a vector composed of promoter, ribosome binding sequence, the DNA encoding the protein or protein complex of the present invention and a transcription termination sequence. The recombinant DNA may contain a gene regulating the promoter.

The expression vector includes, for example, pHelix1 (manufactured by Roche Diagnostics), pKK233-2 (manufactured by Amersham Pharmacia Biotech), pSE280 (manufactured by Invitrogen Corporation), pGEMEX-1 (manufactured by Promega Corporation), pQE-8 (manufactured by Qiagen), pKYP10 (Japanese Published Unexamined Patent Application No.110600/1983, U.S. Pat. No. 4,686,191), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II KS(–) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM B-400), Japanese Published Unexamined Patent Application No.221091/1985, U.S. Pat. No. 4,868,125], pGKA2 [prepared from *Escherichia coli* IGKA2 (FERM BP-6798), Japanese Published Unexamined Patent Application No.221091/1985, U.S. Pat. No. 4,868,125], pTerm2 (U.S. Pat. Nos. 4,686,191, 4,939,094, 5,160,735), pSupex, pUB110, pTP5, pC194, pEG400 [J. Bacteriol., 172, 2392 (1990)], pGEX (manufactured by Amersham Pharmacia Biotech), pET system (manufactured by Novagen) and pSupex. Additionally, expression vectors with autonomous replication potencies in microorganisms of genus *Corynebacterium* include for example pCG1 (Japanese Published Unexamined Patent Application No.134500/1983); pCG2 (Japanese Published Unexamined Patent Application No.35197/1983); pCG4 and pCG11 (both in Japanese Published Unexamined Patent Application No.183799/1982, U.S. Pat. No. 4,500,640); pCE54 and pCB101 (both in Japanese Published Unexamined Patent Application No.105999/1983, U.S. Pat. No. 4,710,471); pCE51, pCE52 and pCE53 [all in Mol. Gen. Genet., 196, 175 (1984)]; pAJ1844 (Japanese Published Unexamined Patent Application No.21614/1983, U.S. Pat. No. 4,514,502); pHK4 (Japanese Published Unexamined Patent Application No.20399/1995, U.S. Pat. No. 5,616,480); pHM1519 [Agric. Biol. Chem., 48, 2901, (1985)]; pCV35 and pECM1 [both in J. Bacteriol., 172, 1663 (1990)]; pC2 [Plasmid, 36, 62 (1996)] and the like.

As the promoter, any promoter from which a gene can be expressed in the host cell can be used. For example, promoters derived from *Escherichia coli* and phages, such as trp promoter ($P_{trp}$) lac promoter, $P_L$ promoter, $P_R$ promoter and T7 promoter are mentioned. Additionally, artificially designed and modified promoters can also be used, such as two aligned $P_{trp}$ promoters in series ($P_{trp} \times 2$), tac promoter, lacT7 promoter, and let I promoter. Still additionally, the promoter capable of functioning in bacteria of the genus *Corynebacterium* [Microbiology, 142, 1297 (1996), Appl. Microbiol. Biotechnol., 53, 674 (2000)]) and the like can also be used.

A plasmid with the distance between the ribosome binding sequence, namely the Shine-Dalgarno sequence and the initiation codon as adjusted to an appropriate length (for example, 6 to 18 bases) is preferably used.

By modifying the nucleotide sequence of the region encoding the protein or protein complex of the present invention to make codons optimum for the expression in hosts, the productivity of the objective protein or protein complex can be improved.

For the recombinant vector of the present invention, a transcription termination sequence is not necessarily required for the expression of the DNA of the present invention. However, it is preferred that a transcription termination sequence is arranged immediately downstream the structural gene.

The host cell includes microorganisms of the genera *Escherichia, Serratia, Bacillus, Brevibacterium, Corynebacterium, Microbacterium* and *Pseudomonas*, for example, *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Serratia ficaria, Serratia fonticola, Serratia liquefaciens, Serratia marcescens, Bacillus subtilis, Bacillus amyloliquefacines, Brevibacterium immariophilum* ATCC14068, *Brevi-* bacterium saccharolyticum ATCC14066, *Brevibacterium flavum* ATCC14067, *Brevibacterium lactofermentum* ATCC13869, *Corynebacterium ammoniagenes* ATCC6872, *Corynebacterium ammoniagenes* ATCC21170, *Corynebacterium glutamicum* ATCC13032, *Corynebacterium acetoacidophilum* ATCC13870, *Microbacterium ammoniaphilum* ATCC15354 and *Pseudomonas* sp. D-0110.

As the method for transformation with the recombinant DNA, any method to introduce DNA into the host cell can be used, including, for example, the method using calcium ion [Proc. Natl. Acad. Sci. USA, 69, 2110 (1972)], protoplast method [Japanese Published Unexamined Patent Application No.248394/1988, Japanese Published Unexamined Patent Application No.186492/1982, U.S. Pat. No. 4,683,205, Japanese Published Unexamined Patent Application No.56678/1983, U.S. Pat. No. 4,681,847, J. Bacteriol., 159, 306 (1984)], electroporation method (Japanese Published Unexamined Patent Application No.207791/1990) or the methods described in Gene, 17, 107 (1982) and Mol. Gen. Genet., 168, 111 (1979) are mentioned. Otherwise, a DNA library of the chromosome of a microorganism of the genus *Corynebacterium* is prepared by using *Escherichia coli*, then DNA is transferred from *Escherichia coli* to a microorganism of the genus *Corynebacterium* via conjugation according to known methods [J. Bacteriol. 172, 1663 (1990), J. Bacteriol. 178, 5768 (1996)].

In case that yeast is used as the host cell, the expression vector includes, for example, YEp13 (ATCC37115), YEp24 (ATCC37051) and YCp50 (ATCC37419).

As the promoter, any promoter from which a gene can be expressed in yeast strains can be used, including, for example, the promoter of the gene of the glycolytic pathway such as hexokinase, PHO5 promoter, PGK promoter, GAP promoter, ADH promoter, gal 1 promoter, gal 10 promoter, heat shock protein promoter, MFα1 promoter and CUP 1 promoter.

The host cell includes, for example, microorganisms of the genus *Saccharomyces, Kluyveromyces, Trichosporon* or *Schwanniomyces*, for example, *Saccharomyces cerevisiae, Schizosaccharomyces pombe, Kluyveromyces lactis, Trichosporon pullulans* and *Schwanniomyces alluvius*.

As the method for transformation with the recombinant DNA, any method to introduce DNA into yeast can be used, including, for example, electroporation method [Methods. Enzymol., 194, 182 (1990)], spheroplast method [Proc. Natl. Acad. Sci. USA, 84, 1929 (1978)], lithium acetate method [J. Bacteriology, 153, 163 (1983)], and the method described in Proc. Natl. Acad. Sci. USA, 75, 1929 (1978).

In case that an animal cell is used as the host cell, the expression vector includes, for example, pcDNAI, pcDM8 (commercially available from Funakoshi Co., Ltd.), pAGE107 [Japanese Published Unexamined Patent Application No.22979/1991, U.S. Pat. No. 516,735; Cytotechnology, 3, 133, (1990)], pAS3-3 (Japanese Published Unexamined Patent Application No.227075/1990, U.S. Pat. No. 5,218,092), pCDM8 [Nature, 329, 840, (1987)], pcDNAI/Amp (manufactured by Invitrogen Corporation), pREP4 (manufactured by Invitrogen Corporation), pAGE103 [J. Biochemistry, 101, 1307 (1987)] and pAGE210.

As the promoter, any promoter from which a gene can be expressed in animal cells can be used, including, for example, the promoter of the immediate early (IE) gene of cytomegalovirus (CMV), the SV40 early promoter, the promoter of retrovirus, metallothionein promoter, heat shock promoter and SRα promoter. Additionally, an enhancer of the IE gene of human CMV can be used together with such promoters.

The host cell includes Namalwa cell as a human cell, COS cell as a monkey-cell, CHO cell as Chinese hamster cell, HBT5637 (Japanese Published Unexamined Patent Application No.299/1988, ATCC No. ATB-9) and the like.

As the method for transformation with the recombinant vector, any method to introduce DNA into animal cells can be used, including, for example, electroporation method [Cytotechnology, 3, 133 (1990)], calcium phosphate method (Japanese Published Unexamined Patent Application No.227075/1990, U.S. Pat. No. 5,218,092) and lipofection method [Proc. Natl. Acad. Sci. USA, 84, 7413 (1987)].

In case that insect cells are used as the host cells, the protein or protein complex of the present invention can be expressed by methods described in, for example, Current Protocols in Molecular Biology, Baculovirus Expression Vectors, A Laboratory Manual, W. H. Freeman and Company, New York (1992) and Bio/Technology, 6, 47 (1988).

Specifically, a recombinant virus is recovered in the culture supernatant of an insect cell via co-transfection of the insect cell with the recombinant gene transfer vector and baculovirus; further, an insect cell is infected with the recombinant virus, to express the protein or protein complex of the present invention.

The gene transfer vector for use in the method includes, for example, pVL1392, pVL1393 and pBlueBacIII (all manufactured by Invitrogen Corporation).

As the baculovirus, for example, *Autographa californica* nuclear polyhedrosis virus can be used as a virus which infects insects of the family *Noctuidae*.

As the insect cells, Sf9 and Sf21 as the ovarian cells of *Spodoptera frugiperda* [Baculovirus Expression Vectors, A Laboratory Manual, W. H. Freeman and Company, N.Y. (1992)] and High 5 as the ovarian cell of *Trichoplusia ni* (manufactured by Invitrogen Corporation) can be used.

The method for the co-transfection of the insect cells with the recombinant gene transfer vector and the baculovirus for the preparation of the recombinant virus, includes, for example, the calcium phosphate method (Japanese Published Unexamined Patent Application No.227075/1990, U.S. Pat. No. 5,218,092) and the lipofection method [Proc. Natl. Acad. Sci. USA, 84, 7413 (1987)].

In case that plant cells are used as the host cells, the expression vector includes, for example, Ti plasmid and tobacco mosaic virus vector.

As the promoter, any promoter including, for example, the 35S promoter of cauliflower mosaic virus (CaMV) and rice actin 1 promoter can be used, as long as a gene can be expressed from the promoter in plant cells.

The host cell includes plant cells of, for example, tobacco, potato, tomato, carrot, soybean, rape, alfalfa, rice, wheat, and barley.

As the method for transformation with the recombinant DNA, any method for introducing DNA into plant cells can be used, including, for example, the method using *Agrobacterium* (Japanese Published Unexamined Patent Application No.140885/1984, Japanese Published Unexamined Patent Application No. 70080/1985 and WO 94/00977), the electroporation method (Japanese Published Unexamined Patent Application No.251887/1985) and the method using particle gun (Japanese Patent No. 2606856 and Japanese Patent No. 2517813).

As the method for expressing the gene, secretory expression, or fusion protein expression or the like can be carried out according to the method described in Molecular Cloning, Second edition, in addition to direct expression.

In case of the expression in yeast, animal cells, insect cells or plant cells, a protein or protein complex with addition of sugar or sugar chain can be recovered.

The protein or protein complex of the present invention can be produced by culturing the transformant thus constructed in a culture medium to allow the transformant to express and accumulate the protein or protein complex of the present invention in the culture and recovering the protein or protein complex from the culture. Culturing the transformant of the present invention in a culture medium can be carried out according to a usual method to be applied for in culturing hosts.

As the culture medium for culturing the transformant obtained by using bacteria such as *Escherichia coli* or eukaryotic organisms such as yeast as the hosts, any of natural and synthetic culture media containing carbon sources, nitrogen sources, inorganic salts and the like, which can be assimilated by the biological organism and in which the transformant can be cultured efficiently can be used.

As the carbon source, any carbon source assimilated by the biological organism can be used, such as carbohydrates such as glucose, fructose, sucrose, molasses containing these substances, starch or starch hydrolyzates; organic acids such as acetic acid and propionic acid; and alcohols such as ethanol and propanol.

As the nitrogen source, ammonia, ammonium salts of inorganic acids or organic acids, such as ammonium chloride, ammonium sulfate, ammonium acetate and ammonium phosphate; other nitrogen-containing compounds; and peptone, meat extract, yeast extract, corn steep liquor, casein hydrolyzates, soy bean bran, soy bean bran hydrolyzates, various fermenting bacteria and digested products thereof and the like can be used.

As the inorganic salts, potassium dihydrogen phosphate, dipotassium hydrogen phosphate, magnesium phosphate, magnesium sulfate, sodium chloride, ferrous sulfate,. manganese sulfate, copper sulfate and calcium carbonate and the like can be used.

The culturing is generally carried out under aerobic conditions, by shaking culture or submerged aeration agitation culture. The culturing temperature is preferably 15 to 40° C., and the culturing period is generally 16 hours to 7 days. The pH during the culturing is retained at 3.0 to 9.0. The pH is adjusted with inorganic or organic acids, alkali solutions, urea, calcium carbonate, ammonia and the like.

Additionally, antibiotics such as ampicillin and tetracycline can be added to the culture medium if required.

For culturing a microorganism transformed with a recombinant vector where an inducible promoter is used as promoter, an inducer can be added if required. For example, for culturing a microorganism transformed with a recombinant vector where lac promoter is used, isopropyl-β-D-thiogalactopyranoside and the like can be added to the culture medium, and for culturing a microorganism transformed with a recombinant vector where trp promoter is used, indole acrylic acid and the like can be added to the culture medium.

As the culture medium for culturing a transformant obtained by using an animal cell as the host, culture media for general use, such as RPMI 1640 medium [The Journal of the American Medical Association, 199, 519 (1967)], Eagle's MEM [Science, 122, 501 (1952)], Dulbecco's modified MEM [Virology, 8, 396 (1959)], 199 medium [Proceeding of the Society for the Biological Medicine, 73, 1 (1950)] or culture media prepared by adding fetal calf serum to these culture media can be used.

The culturing is generally carried out under conditions, such as at pH 6 to 8 and 30 to 40° C. in the presence of 5% $CO_2$ for one to 7 days.

Additionally, antibiotics such as kanamycin and penicillin can be added to the culture medium during the culturing if required.

As the culture medium for culturing a transformant obtained by using an insect cell as the host, TNM-FH medium (manufactured by Pharmingen); Sf-900 II SFM (manufactured by Life Technologies); ExCell 400 and ExCell 405 (both manufactured by JRH Biosciences, Co.); Grace's Insect Medium [Nature, 195, 788 (1962)]; and the like can be used.

The culturing is generally conducted under conditions, for example at pH 6 to 7 and 25 to 30° C. for one to 5 days.

Additionally, antibiotics such as gentamycin can be added to the culture medium if reqired.

A transformant obtained by using a plant cell as the host can be cultured as a cell or after differentiation into a differentiated plant cell or a plant organ. As the culture medium for culturing the transformant, Murashige and Skoog (MS) medium, White's medium, or culture media prepared by adding plant hormones such as auxin and cytokinin or the like to these culture media can be used.

The culturing is generally conducted under conditions, for example at pH 5 to 9 and 20 to 40° C. for 3 to 60 days.

Additionally, antibiotics such as kanamycin and hygromycin can be added to the culture medium if required.

As described above, the protein or protein complex of the present invention can be produced, by culturing a microorganism-, animal cell- or plant cell-derived transformant carrying the recombinant DNA into which the DNA encoding the protein or protein complex of the present invention is inserted by general culturing methods, to allow the transformant to express and accumulate the protein or protein complex and recovering the protein or protein complex from the culture.

As the method for expressing the gene, secretory expression or expression as a fusion protein can be carried out according to the method described in Molecular Cloning, Second edition, in addition to direct expression.

The method for expressing the protein or protein complex of the present invention includes a method for expressing inside host cells, a method for secreting outside host cells, and a method for expressing on the outer membrane of host cells. By changing a host cell to be used or modifying the structure of the protein to be expressed, the method can be selected.

In case that the protein or protein complex of the present invention is expressed inside the host cell or on the outer membrane of the host cell, the protein or protein complex can be secreted outside the host cell, according to the method of Paulson, et al. [J. Biol. Chem., 264, 17619 (1989)], the method of Law, et al. [Proc. Natl. Acad. Sci., USA, 86, 8227 (1989), Genes Develop., 4, 1288 (1990)], or the methods described in Japanese Published Unexamined Patent Application No.336963/1993, WO 94/23021 and the like.

Specifically, the protein or protein complex of the present invention can be secreted outside the host cell, by expressing the protein or protein complex of the present invention in a form such that signal peptide is added to a protein containing the active site of the protein or protein complex of the present invention, by means of the genetic engineering.

According to the method described in Japanese Published Unexamined Patent Application No.227075/1990 (U.S. Pat. No. 5,218,092), the productivity can be improved by utilizing gene amplification systems using dihydrofolate reductase genes and the like. So as to isolate and purify the protein or protein complex of the present invention from the culture of the transform ant, general methods for isolation and purification of enzymes can be used.

In case that the protein or protein complex of the present invention is expressed, for example, in the soluble state inside a cell, the cell is recovered by centrifugation after culturing and is then suspended in an aqueous buffer, which is subsequently disrupted with an ultrasonicator, French press, Manton-Gaulin homogenizer, Dinomill and the like, to recover a cell-free extract. From the supernatant recovered by centrifuging the cell-free extract, a purified product sample can be isolated using known methods to isolate and purify enzymes, including, for example, solvent extraction, salting out with ammonium sulfate, desalting, precipitation with organic solvents, anion exchange chromatography using resins such as diethylaminoethyl (DEAE)-Sepharose, DIAION HPA-75 (manufactured by Mitsubishi Chemical Industry, Co.), cation exchange chromatography using resins such as S-Sepharose FF (manufactured by Amersham Pharmacia Biotech, Co.), hydrophobic chromatography using resins such as phenyl Sepharose, gel filtration method using molecular sieve, affinity chromatography, chromatofocusing, electrophoresis such as isoelectric focusing, singly or in combination.

In case that the protein or protein complex is expressed in the form of an inclusion body inside a cell, the cell is recovered and disrupted in the same manner as descrived above, followed by centrifugation to recover a precipitate fraction, from which the protein or protein complex is recovered by known methods. The inclusion body of the protein or protein complex is solubilized with a protein denaturant. The protein-solubilized solution is diluted with or dialyzed to against a solution without protein denaturant or a solution where the concentration of the protein denaturant is at lower level not to denature the protein or protein complex, to refold the protein or protein complex in a normal tertiary structure. Subsequently, the resulting protein or protein complex is subjected to the same method for isolation and purification as described above, to isolate a purified product sample.

In case that the protein or protein complex of the present invention or derivatives thereof such as a glycosylated form are secreted extracellularly, the protein or protein complex or the derivatives thereof, such as a glycosylated form, can be recovered in the culture supernatant. More specifically, the culture is treated by the same means as described above, such as centrifugation, to recover the soluble fraction, from which a purified product sample can be isolated by the method for isolation and purification as described above.

[3] Production of Nucleoside 5'-triphosphate

Using as an enzyme source the culture of the transformant prepared described above in [2] or a treated product of the culture, nucleoside 5'-triphosphate can be produced by reacting a precursor of nucleoside 5'-triphosphate with the enzyme source in an aqueous medium.

The treated product of the culture includes, for example, a concentrate of the culture, a dried product of the culture, transformant cells recovered by centrifuging the culture, a dried product of the transformant cells, a freeze-dried product of the transformant cells, a detergent-treated product of the transformant cells, a sonicated product of the transformant cells, a mechanically disrupted product of the transformant cells, a solvent-treated product of the transformant cells, a enzyme-treated product of the transformant cells, a protein fraction of the transformant cells, an immobilized product of the transformant cells or an enzyme sample extracted from the transformant cells.

As the enzyme source for generating nucleoside 5'-triphosphate, the transformant cells are used at a concentration of 1 g/liter to 500 g/liter, preferably 10 g/liter to 300 g/liter based on wet weight.

The precursor of nucleoside 5'-triphosphate includes, for example, adenine, guanine, uracil, cytosine, hypoxanthine, adenosine, guanosine, uridine, cytidine, inosine, adenosine 5'-monophosphate, guanosine 5'-monophosphate, uridine 5'-monophosphate, cytidine 5'-monophosphate, and inosine 5'-monophosphate.

The nucleoside 5'-triphosphate includes for example adenosine 5'-triphosphate, guanosine 5'-triphosphate, uridine 5'-triphosphate, and cytidine 5'-triphosphate.

The aqueous medium for use in generating nucleoside 5'-triphosphate includes, for example, water; buffers such as phosphate buffer, carbonate buffer, acetate buffer, borate buffer, citrate buffer and Tris buffer; alcohols such as methanol and ethanol; esters such as ethyl acetate; ketones such as acetone; and amides such as acetamide. Additionally, the liquid culture of the microorganism used as the enzyme source can also be used as the aqueous medium.

For the generation of nucleoside 5'-triphosphate, a detergent or an organic solvent can be added if required. As the detergent, any of detergents promoting the generation of nucleoside 5'-triphosphate can be used, including, for example, nonionic detergents such as polyoxyethylene octadecylamine (for example, Nymeen S-215, manufactured by Nippon Oil & Fats Co., Ltd.), cationic detergents such as cetyltrimethylammonium bromide and alkyldimethyl benzylammonium chloride (for example, Cation F2–40E, manufactured by Nippon Oil & Fats Co., Ltd.) and anionic detergents such as lauroyl sarcosinate and tertiary amines such as alkyldimethylamine (for example, tertiary amine FB, manufactured by Nippon Oil & Fats Co., Ltd.), singly or in combination of several types thereof. The detergent is generally used at a concentration of 0.1 to 50 g/liter. The organic solvent includes, for example, xylene, toluene, aliphatic alcohol, acetone and ethyl acetate and is generally used at a concentration of 0.1 to 50 ml/liter.

The nucleoside 5'-triphosphate generating reaction is carried out in an aqueous medium under conditions of pH 5 to 10, preferably pH 6 to 8 and 20 to 60° C., for one to 96 hours. For the generating reaction, inorganic salts such as magnesium chloride can be added if required.

The nucleoside 5'-triphosphate generated in an aqueous medium is determined by known methods (for example, WO 98/12343) using HPLC.

The nucleoside 5'-triphosphate generated in the reaction solution can be isolated by known methods using activated charcoal, ion exchange resins and the like.

The present invention is illustrated in the following examples, but the present invention is not limited to these examples.

EXAMPLE 1

Preparation of the Chromosomal DNA of *Corynebacterium Ammoniagenes* Strain ATCC6872

*Corynebacterium ammoniagenes* strain ATCC6872 was inoculated in 8 ml of a culture medium prepared by adding glycine (10 mg/ml) to CM medium (10 mg/ml polypeptone, 10 mg/ml meat extract, 5 mg/ml yeast extract, 3 mg/ml sodium chloride, 30 µg/ml biotin, pH7.2), for culturing at 30° C. overnight.

After culturing, the cells were collected from the resulting culture via centrifugation.

The cells were washed with TE buffer [10 mmol/liter Tris-HCl, 1 mmol/liter ethylenediaminetetraacetic acid (EDTA), pH8.0] and subsequently suspended in 800 µl of the same buffer. To the suspension were added 40 µl of 50 mg/ml lysozyme solution and 20 µl of 10 mg/ml RNase A solution, and the resulting solution was incubated at 37° C. for one hour. To the resulting solution was added 20 µl of 20% sodium dodecylsulfate (SDS) solution, and the resulting solution was incubated at 70° C. for one hour. 24 µl of 20 mg/ml proteinase K solution was added to the resulting reaction solution, and the resulting solution was incubated at 50° C. for one hour. To the resulting reaction solution was added an equal volume of phenol, followed by agitation. The resulting solution was left to stand overnight at 4° C., to extract DNA into the aqueous layer. The aqueous layer was then recovered. To the aqueous layer was added an equal volume of phenol/chloroform, followed by agitation and extraction for 2 hours, and the resulting aqueous layer was recovered. To the resulting aqueous layer was added an equal volume of chloroform/isoamyl alcohol, followed by agitation and extraction for 30 minutes, and the resulting aqueous layer was recovered. To the aqueous layer was added a 2-fold volume of ethanol, to precipitate DNA. The resulting precipitate was dissolved in 300 µl of TE buffer, and the resulting solution was used as chromosomal DNA.

EXAMPLE 2

Probe-labeling

According to the method described in Current Protocols in Molecular Biology, chromosomal DNA was prepared from *Escherichia coli* strain W3110. The DNA primer of SEQ ID NO: 17 and the DNA primer of SEQ ID NO: 18, corresponding to parts of the gene coding for the β subunit of *Escherichia coli* $F_0F_1$-ATPase, were synthesized using the DNA synthesizer of Model 8905, manufactured by Perceptive Biosystems, Co. Using the synthesized DNAs as primers and the chromosomal DNA of *Escherichia coli* strain W3110 as a template, the probe was labeled by PCR DIG Probe Synthesis Kit (manufactured-by Roche Diagnostics KK). Labeling reaction was carried out according to the manual of the-kit, using 0.1 µg of the chromosomal DNA and 0.5 pmol of each of the primers in 50 µl of the reaction solution, and reaction step of 94° C. for 30 seconds, of 55° C. for one minute and of 72° C. for one minute were repeated 30 times.

EXAMPLE 3

Southern Hybridization

10 µg of the chromosomal DNA as isolated in Example 1was completely digested with restriction endonuclease EcoRI. Similarly, the chromosome was thoroughly cleaved with BamHI. 1 µg each of the samples cleaved with the respective restriction endonucleases was subjected to agarose gel electrophoresis. After electrophoresis, the DNA was transferred onto nylon membrane according to the method described in Molecular Cloning, Second edition.

Hybridization was carried out by using DIG Luminescent Detection Kit (manufactured by Roche Diagnostics KK.). The nylon membrane (Hybond N+) with the DNA transferred thereon was subjected to prehybridization in 1 ml of prehybridization solution [0.5 mol/liter $Na_2HPO_4$-$12H_2O$ (pH7.2), 7% SDS, 1 mmol/liter EDTA] per 10 $cm^2$ of membrane at 65° C. for 30 minutes. Then, 1 ml of a prehybridization solution containing 1 µl of the probe prepared in Example 2 per 3 ml of the solution was used per 5 $cm^2$ of membrane, for hybridization at 65° C. for 16 hours. After the hybridization, the membrane was washed with a wash buffer [40 mmol/liter $Na_2HPO_4$-12 $H_2O$ (pH 7.2), 1% SDS] at 65° C. for 20 minutes. The wash procedure was repeated three times. Then, the treatment using 1 ml of DIG Buffer 1 [100 mmol/liter Tris-HCl (pH7.5), 150 mmol/liter NaCl] per 2 $cm^2$ of membrane at room temperature for 10 minutes was repeated twice. Subsequently, blocking against antibodies was carried out, using 0.5 w/v % blocking solution at room temperature for.one hour. Labeling with an antibody was carried out at room temperature, using 62.5 µl of DIG. Buffer 1 containing 75 mU/ml anti-DIG AP Fab fragment and 0.2% Tween 20 per 1 $cm^2$ of membrane for 30 minutes. Additionally, wash procedure using DIG Buffer 1 containing 0.2% Tween 20 at a ratio of 0.125 ml per 1 $cm^2$ of membrane at room temperature for 15 minutes was repeated twice. Subsequently, the membrane was treated with DIG Buffer 3 [100 mmol/liter Tris-HCl (pH9.5), 100 mmol/liter NaCl, 50 mmol/liter $MgCl_2$] for 3 minutes. After dropwise addition of CSPD solution, the resulting mixture was incubated at 37° C. for 15 minutes, luminescent reaction was promoted.

After termination of the luminescent reaction, the membrane was dried in air. Subsequently, the membrane was exposed to an X-ray film for 30 minutes.

As a result of hybridization, the probe strongly hybridized with the EcoRI-cleaved 6.5-Kb fragment and the BamHI-cleaved 6-Kb fragment of *Corynebacterium ammoniagenes* chromosomal DNA.

EXAMPLE 4

Colony Hybridization 1 µg of *Corynebacterium ammoniagenes* ATCC6872 chromosomal DNA was completely digested with restriction endonuclease EcoRI or BamHI, and the individual digested fragments were separated by agarose gel electrophoresis to recover fragments around the EcoRI-cleaved 6.5-kb fragment and the BamHI-cleaved 6-Kb fragment, by RECOCHIP (manufactured by Takara Shuzo Co., Ltd.). 0.1 µg of a plasmid vector pBluescript II KS (−) (manufactured by Stratagene) was thoroughly digested with EcoRI or BamHI, which was then subjected to dephosphorylation reaction with temperature-sensitive alkaliphosphatase (manufactured by GIBCO BRL).

The EcoRI cleavage fragment around 6.5 kb and the EcoRI-cleaved and phosphatase-treated pBluescript II KS (−) were subjected to a ligation reaction at 16° C. for 16 hours, using a ligation kit. Using the ligation reaction solution, *Escherichia coli* strain JM109 was, transformed by the method using calcium ion described in Molecular Cloning, Second edition. The resulting transformant was spread on an LB agar medium containing 100 µg/ml ampicillin, for overnight culturing at 37° C. Similarly, the BamHI cleavage fragment around 6 kb and the BamHI-cleaved and phosphatase-treated pBluescript II KS (−) were subjected to a ligation reaction at 16° C. for 16 hours, using a ligation kit. Using the ligation reaction solution, the *Escherichia coli* strain JM109 was transformed by the method described above. The resulting transformant was spread on an LB agar culture medium containing 100 µg/ml ampicillin, for overnight culturing at 37° C. The growing colony was transferred on the membrane (Hybond N+) and lysed to fix the DNA on the membrane according to the method described in Molecular Cloning, Second edition. Colony hybridization was carried out by the same method as for Southern hybridization in Example 3.

Consequently, a bacterial strain harboring the plasmid pE61 carrying the 6.5-kb EcoRI cleavage fragment of Corynebacterium ammoniagenes ATCC6872 chromosomal DNA and a bacterial strain harboring the plasmid pDW31 carrying the 6-kb BamHI cleavage fragment thereof were selected as positive clones.

From the colonies of the two clones were isolated the plasmids, which were the plasmids pE61 and pDW31, so that the structures of the plasmids were confirmed by digestion with restriction endonucleases (FIG. 1).

EXAMPLE 5

Recovery of Upstream Gene

The plasmids pE61 and pDW31 as obtained in Example 4 were found not to carry the genes predicted to be present, upstream among the genes coding for the proteins composing the $F_0F_1$-ATPase protein complex. Therefore, the genes present upstream were isolated by the following method.

The DNA primer having the nucleotide sequence represented by SEQ ID NO: 19 and the DNA primer having the nucleotide sequence represented by SEQ ID NO: 20, corresponding to parts of the $F_0F_1$-ATPase b subunit gene which exists in the plasmid pE61, were synthesized using a DNA synthesizer of Model 8905, which was manufactured by Perceptive Biosystems, Co. Using the synthesized DNAs as primers and the plasmid pE61 DNA as a template, the probe was labeled by PCR DIG Probe Synthesis Kit (manufactured by Roche Diagnostics). Using the resulting probe, Southern hybridization was carried out by the same method as in Example 3. Strong hybridization with a 5.0-Kb, HindIII-digested fragment of the chromosomal DNA of Corynebacterium ammoniagenes strain ATCC6872 was observed.

Using a bacterial strain harboring a plasmid constructed by inserting a fragment of the HindIII-digested chromosome DNA around 5.0 kb into pBluescript II KS (-), colony hybridization was carried out. Then, a bacterial strain harboring a plasmid pUH71 carrying a Hind III fragment of 5-kb was hybridized strongly and thus, was selected as a positive clone.

From the colony of the clone was isolated the plasmid, which was named pUH71. Then, the structure of the plasmid was confirmed by digestion with restriction endonucleases. (FIG. 1)

EXAMPLE 6

Determination of a Nucleotide Sequence

The nucleotide sequences of the inserted fragments in the plasmids pE61 and the pDW31 and in the plasmid pUH71 were determined with ABI 377 Sequencer. Open reading frames consisting of individual nucleotide sequences represented by each of SEQ ID NOS: 9 to 16 encoding the amino acid sequences represented by each of SEQ ID NOS: 1 to 8, respectively, existed in the nucleotide sequences of the fragments.

As a result of comparative analysis the nucleotide sequences of the fragments with other bacterial $F_0F_1$-ATPase genes, it is shown that the nucleotide sequences correspond to an operon of genes of the subunits a, c, b, δ, α, γ, β and ε located in this order, as in many other bacteria. The nucleotide sequence of the operon is shown as SEQ ID NO: 21.

Further, Table 1 shows the amino acid sequence identity (%) of each subunit of Bacillus subtilis $F_0F_1$-ATPase [J. Bacteriol., 176, 6802 (1994)] and each subunit of Escherichia coli $F_0F_1$-ATPase [Biochem. J., 224, 799 (1984)] with each subunit of the $F_0F_1$-ATPase of the present invention, respectively.

TABLE 1

| | subunits | | | | | | | |
|---|---|---|---|---|---|---|---|---|
| | a | b | c | α | β | γ | δ | ε |
| Bucillus subtilis | 26 | 29 | 47 | 54 | 65 | 35 | 24 | 31 |
| Escherichia coli | 23 | 31 | 35 | 48 | 61 | 38 | 24 | 32 |

What is claimed is:

1. An isolated DNA comprising one DNA selected from each of the following eight groups:

Group 1 consisting of a DNA of the following ONAs 1(*a*) and 1(*b*):
1(*a*): a DNA having the nucleotide sequence of SEQ ID NO: 9; and
1(*b*): a DNA being at least 95% identical to the DNA having the nucleotide sequence of SEQ ID NO: 9, and which encodes a protein that when combined with all individual proteins having the amino acid sequence each of SEQ ID NOS: 2 to 8 forms, a protein complex having $F_0F_1$-ATPase activity:

Group 2 consisting of the following DNAs 2(*a*) and 2(*b*):
2(*a*): a DNA having the nucleotide sequence of SEQ ID NO: 10; and
2(*b*): a DNA being at least 95% identical to the DNA having the nucleotide sequence of SEQ ID NO: 10, and which encodes a protein that when combined with all individual proteins having the amino acid sequence each of SEQ ID NO: 1 and SEQ ID NOS: 3 to 8 forms, a protein complex having $F_0F_1$-ATPase activity;

Group 3 consisting of the following DNAs 3(*a*) and 3(*b*):
3(*a*): a DNA having the nucleotide sequence of SEQ ID NO: 11; and
3(*b*): a DNA being at least 95% identical to the DNA having the nucleotide sequence of SEQ ID NO: 11, and which encodes a protein that when combined with all individual proteins having the amino acid sequence each of SEQ ID NOS: 1 to 2 and SEQ ID NOS: 4 to 8 forms, protein complex having $F_0F_1$-ATPase activity;

Group 4 consisting of the following DNAs 4(*a*) and 4(*b*):
4(*a*): a DNA having the nucleotide sequence of SEQ ID NO:12; and
4(*b*): a DNA being at least 95% identical to the DNA having the nucleotide sequence of SEQ ID NO: 12, and which encodes a protein that is when combined with all individual proteins having the amino acid sequence each of SEQ ID NOS: 1 to 3 and SEQ ID NOS: 5 to 8 forms, a protein complex having $F_0F_1$-ATPase activity;

Group 5 consisting of the following DNAs 5(*a*) and 5(*b*):
5(*a*): a DNA having the nucleotide sequence of SEQ ID NO:13; and
5(*b*): a DNA being at least 95% identical to the DNA having the nucleotide sequence of SEQ ID NO: 13, and which encodes a protein that when combined with all individual proteins having the amino acid sequence each of SEQ ID NOS: 1 to 4 and SEQ ID NOS: 6 to 8 forms, a protein complex having $F_0F_1$-ATPase activity;

Group 6 consisting of the following DNAs 6(*a*) and 6(*b*):
6(*a*): a DNA having the nucleotide sequence of SEQ ID NO: 14; and
6(*b*): a DNA being at least 95% identical to the DNA having the nucleotide sequence of SEQ ID NO: 14, and which encodes a protein that 7 and 8 to form with when combined with all individual proteins having the amino acid sequence each of SEQ ID NOS: 1 to 5 and SEQ ID NOS: 7 and 8 forms, a protein complex having $F_0F_1$-ATPase activity;

Group 7 consisting of the following DNAs 7(*a*) and 7(*b*):
7(*a*): a DNA having the nucleotide sequence of SEQ ID NO:15; and
7(*b*): a DNA being at least 95% identical to the DNA having the nucleotide sequence of SEQ ID NO: 15, and which encodes a protein that when cpmbined with all individual proteins having the amion acid sequence each of SEQ ID NOS: 1 to 6 and SEQ ID NO: 8 forms, a protein complex having $F_0F_1$-ATPase activity; and Group 8 consisting of the following DNAs 8(*a*) and 8(*b*):
8(*a*): a DNA having the nucleotide sequence of SEQ ID NO: 16; and
8(*b*): a DNA being at least 95% identical to the DNA having the nucleotide sequence of SEQ ID NO: 16, and which encodes a protein that when combined with all individual proteins having the amino acid sequence each of SEQ ID NOS; 1 to 7 forms, a protein complex having $F_0F_1$-ATPase activity.

2. An isolated DNA having the nucleotide sequences SEQ ID NOS: 9 to 16.

3. An isolated DNA having the nucleotide sequence of SEQ ID NO: 21.

4. The DNA according to claim 1, where the DNA is isolated from a microorganism belonging to the genus *Corynebacterium*.

5. The DNA according to claim 1, where the DNA is isolated from a microorganism of the species *Corynebacterium ammoniapenes*.

6. A recombinant DNA constructed by inserting the DNA according to claim 1 into a vector.

7. A transformant obtained by transformation of a host cell with the recombinant DNA according to claim 6.

8. A transformant according to claim 7, where the host cell is a microorganism of the species *Escherichia coli, Corynebacterium glutamicum* or *Corynebacterium ammoniagenes*.

9. A method for producing a protein complex having $F_0F_1$-ATPase activity, which comprises culturing a transformant obtained by transformation of a host cell with the recombinant DNA according to claim 6 in a culture medium, so as to allow a protein complex having $F_0F_1$-ATPase activity to be expressed and accumulated in the culture and recovering the protein complex from the culture.

10. A recombinant DNA constructed by inserting the DNA according to claim 2 into a vector.

11. A recombinant DNA constructed by inserting the DNA according to claim 3 into a vector.

12. A transformant obtained by transformation of a host cell with the recombinant DNA according to claim 10.

13. A transformant obtained by transformation of a host cell with the recombinant DNA according to claim 11.

14. A method for producing a protein complex having $F_0F_1$-ATPase activity, which comprises culturing a transformant obtained by transformation of a host cell with the recombinant DNA according to claim 10 in a culture medium, so as to allow a protein complex having $F_0F_1$-ATPase activity to be expressed and accumulated in the culture and recovering the protein complex from the culture.

15. A method for producing a protein complex having $F_0F_1$-ATPase activity, which comprises culturing a transformant obtained by transformation of a host cell with the recombinant DNA according to claim 11 in a culture medium, so as to allow a protein complex having $F_0F_1$-ATPase activity to be expressed and accumulated in the culture and recovering the protein complex from the culture.

* * * * *